United States Patent
Sustarich et al.

(10) Patent No.: US 11,369,962 B2
(45) Date of Patent: Jun. 28, 2022

(54) METHOD AND DEVICE FOR TRACKING AND MANIPULATION OF DROPLETS

(71) Applicant: NATIONAL TECHNOLOGY & ENGINEERING SOLUTIONS OF SANDIA, LLC, Albuquerque, NM (US)

(72) Inventors: Jess M. Sustarich, San Francisco, CA (US); Chao Chung Shih, Emeryville, CA (US); Anup Kumar Singh, Danville, CA (US); Philip Gach, Kensington, CA (US)

(73) Assignee: National Technology & Engineering Solutions Of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/521,231

(22) PCT Filed: Oct. 26, 2015

(86) PCT No.: PCT/US2015/057406
§ 371 (c)(1),
(2) Date: Apr. 21, 2017

(87) PCT Pub. No.: WO2016/065365
PCT Pub. Date: Apr. 28, 2016

(65) Prior Publication Data
US 2017/0354973 A1 Dec. 14, 2017

Related U.S. Application Data

(60) Provisional application No. 62/068,595, filed on Oct. 24, 2014.

(51) Int. Cl.
| *B01L 3/00* | (2006.01) |
| *C12N 15/10* | (2006.01) |
| *G01N 35/08* | (2006.01) |
| *B01F 33/302* | (2022.01) |
| *B01F 33/3031* | (2022.01) |
| *B01L 7/00* | (2006.01) |
| *G01N 15/14* | (2006.01) |
| *B01F 101/23* | (2022.01) |

(52) U.S. Cl.
CPC .... *B01L 3/502784* (2013.01); *B01F 33/3021* (2022.01); *B01F 33/3031* (2022.01); *B01L 3/50273* (2013.01); *B01L 3/502738* (2013.01); *B01L 3/502746* (2013.01); *B01L 3/502761* (2013.01); *B01L 7/00* (2013.01); *C12N 15/1058* (2013.01); *G01N 15/1404* (2013.01); *G01N 15/1434* (2013.01); *G01N 35/08* (2013.01); *B01F 2101/23* (2022.01); *B01L 3/502753* (2013.01); *B01L 2200/0605* (2013.01); *B01L 2200/0647* (2013.01); *B01L 2200/0652* (2013.01); *B01L 2200/0673* (2013.01); *B01L 2200/0689* (2013.01); *B01L 2200/10* (2013.01); *B01L 2300/0867* (2013.01); *B01L 2300/0883* (2013.01); *B01L 2300/1805* (2013.01); *B01L 2400/0415* (2013.01); *B01L 2400/0424* (2013.01); *B01L 2400/082* (2013.01); *B01L 2400/086* (2013.01); *G01N 2015/149* (2013.01); *G01N 2015/1413* (2013.01); *G01N 2015/1422* (2013.01)

(58) Field of Classification Search
CPC ........... B01L 3/502784; B01L 3/50273; B01L 3/502746; B01L 7/00; B01L 2200/0647; B01L 2300/0883; B01L 2200/0605; B01L 2200/0652; B01L 2200/0673; B01L 2400/082; B01L 2400/086; B01L 2300/0867; B01F 13/0071; G01N 35/08; G01N 15/1404; G01N 2015/1413; G01N 2015/149
See application file for complete search history.

(56) References Cited

U.S. PATENT DOCUMENTS

| 6,939,451 B2 * | 9/2005 | Zhao | B01L 3/502707 204/451 |
| 8,367,370 B2 | 2/2013 | Wheeler et al. | |
| 2007/0148763 A1 | 6/2007 | Huh et al. | |
| 2008/0003142 A1 * | 1/2008 | Link | B01L 3/565 422/82.08 |
| 2008/0038810 A1 * | 2/2008 | Pollack | B01L 3/502784 435/283.1 |
| 2009/0181864 A1 | 7/2009 | Nguyen et al. | |
| 2011/0008767 A1 | 1/2011 | Durack | |
| 2011/0114190 A1 * | 5/2011 | Wen | B01L 3/0265 137/1 |

(Continued)

FOREIGN PATENT DOCUMENTS

| WO | WO2007120241 | 10/2007 |
| WO | WO 2013/143562 A1 | 10/2013 |

OTHER PUBLICATIONS

International Search Report dated Feb. 5, 2016 for International Patent Application No. PCT/US2015/057406 filed Oct. 26, 2015.

(Continued)

*Primary Examiner* — Sahana S Kaup
(74) *Attorney, Agent, or Firm* — Sheppard, Mullin, Richter & Hampton LLP

(57) ABSTRACT

Disclosed are devices and methods useful for confined-channel digital microfluidics that combine high-throughput droplet generators with digital microfluidic for droplet manipulation. The present disclosure also provides an off-chip sensing system for droplet tracking.

15 Claims, 19 Drawing Sheets

(56) References Cited

U.S. PATENT DOCUMENTS

2013/0028812 A1* 1/2013 Prieto ............... B01L 3/502784
422/502

OTHER PUBLICATIONS

Written Opinion dated Feb. 5, 2016 for International Patent Application No. PCT/US2015/057406 filed Oct. 26, 2015.
Abate et al., "Valve-based flow focusing for drop formation," Applied Physics Letters 2009, 94, 123503-1-12350-3.
Abate et al., "High-throughput injection with microfluidics using picoinjectors," PNAS 2010, 107(45), 19163-19166.
Aebersold et al., "Mass spectrometry-based proteomics," Nature 2003, 422(6928), 198-207.
Ahn et al., "Electrocoalescence of drops synchronized by size-dependent flow in microfluidic channels," Applied Physics Letters 2006, 88(264105), 1-3.
Ahn et al., "On-demand electrostatic droplet charging and sorting," Biomicrofluidics 2011, 024113.
Au et al., "Integrated microbioreactor for culture and analysis of bacteria, algae and yeast," Biomedical Microdevices 2011, 13, 41-50.
Barbulovic-Nad et al., "Digital microfluidics for cell-based assays," Lab Chip 2008, 8, 519-526.
Barbulovic-Nad et al., "A microfluidic platform for complete mammalian cell culture," Lab Chip 2010, 10, 1536-1542.
Boeck et al., "Current status of flow cytometry in cell and molecular biology," International Review of Cytology 2001, 204, 239-298.
Boedicker et al., "Detecting bacteria and determining their susceptibility to antibiotics by stochastic confinement in nanoliter droplets using plug-based microfluidics," Lab Chip 2008, 8(8), 1265-1272.
Brouzes et al., "Droplet microfluidic technology for single-cell high-throughput screening," PNAS 2009, 106(34), 14195-14200.
Elbuken et al., "Detection of microdroplet size and speed using capacitive sensors," Sensors and Actuators, A; Physical 2011, 171(2), 55-62.
Fair et al., "Digital microfluidics: is a true lab-on-a-chip possible?," Microfluidics and Nanofluidics 2007, 3, 245-281.
Huh et al., "A Gravity-Driven Microfluidic Particle Sorting Device with Hydrodynamic Separation Amplification," Analytical Chemistry 2007, 79(4), 1369-1376.
Jebrail et al., "Let's get digital: digitizing chemical biology with microfluidics," Current Opinion in Chemical Biology 2010, 14, 574-581.
Mazutis et al., "Single-cell analysis and sorting using droplet-based microfluidics," Nature Protocols 2013, 8(5), 870-891.
Mousa et al., "Droplet-Scale Estrogen Assays in Breast Tissue, Blood, and Serum," Science Translational Medicine 2009, 1(1), 1-7.
Nagamine et al., "On-Chip Transformation of Bacteria," Analytical Chemistry 2005, 77(13), 4278-4281.
Nguyen et al., "Optical detection for droplet size control in microfluidic droplet-based analysis systems," Sensors and Actuators, B: Chemical 2006, 117, 431-436.
Niu et al., "Real-time detection, control, and sorting of microfluidic droplets," Biomicrofluidics 2007, 1(044101), 1-12.
O'Donovan et al., "Electrode-free picoinjection of microfluidic drops," Lab Chip 2012, 12, 4029-4032.
Sha et al., "Capillary-composited microfluidic device for heat shock transformation of *Escherichia coli*," Journal of Bioscience and Bioengineering 2011, 112(4), 373-378.
Shih et al., "Dried Blood Spot Analysis by Digital Microfluidics Coupled to Nanoelectrospray Ionization Mass Spectrometry," Analytical Chemistry 2012, 84(8), 3731-3738.
Shih et al., "Digital microfluidics with impedance sensing for integrated cell culture and analysis," Biosensors and Bioelectronics 2013, 42, 314-320.
Shim et al., "Simultaneous Determination of Gene Expression and Enzymatic Activity in Individual Bacterial Cells in Microdroplet Compartments," Journal of the American Chemical Society 2009, 131(42), 15251-15256.
Song et al., "Reactions in Droplets in Microfluidic Channels," Angew Chem Int Ed Engl. 2006, 45(44), 7336-7356.
Tan et al., "Design of microfluidic channel geometries for the control of droplet volume, chemical concentration, and sorting," Lab Chip 2004, 4, 292-298.
Teh et al., "Droplet microfluidics," Lab Chip 2008, 8, 198-220.
Wheeler et al., "Putting Electrowetting to Work," Science 2008, 322, 539-540.

* cited by examiner

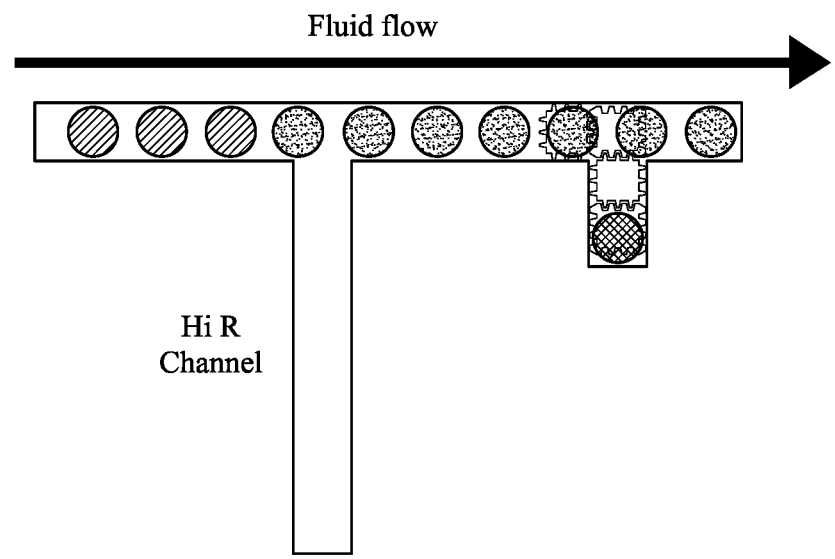
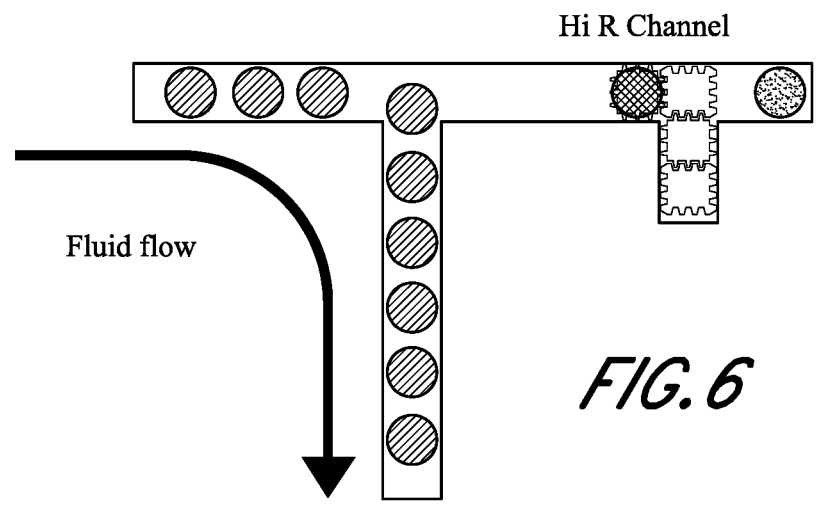
FIG. 6

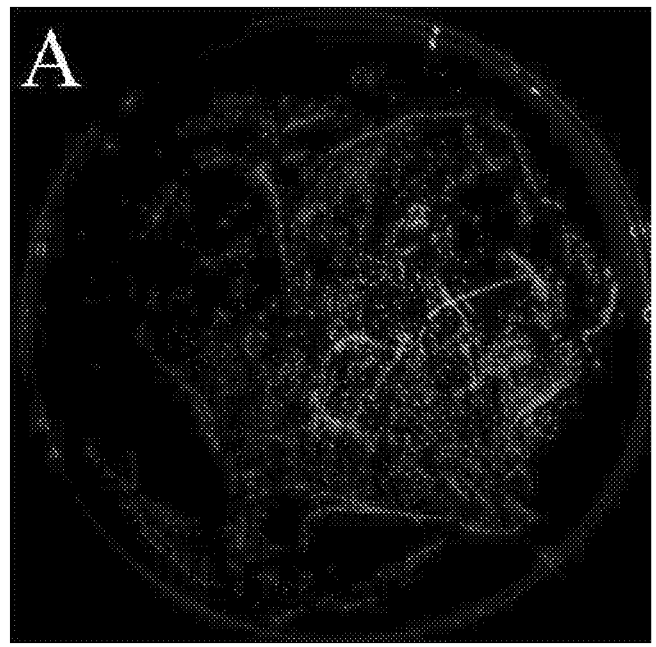
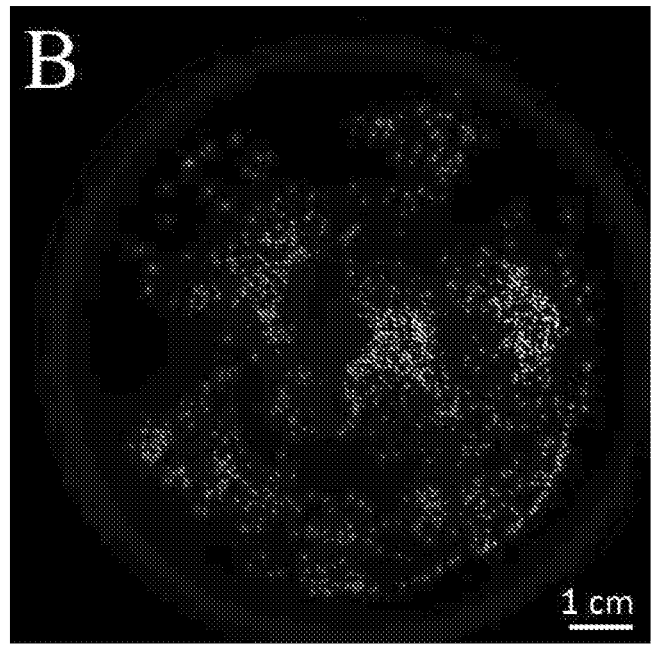
FIG. 11

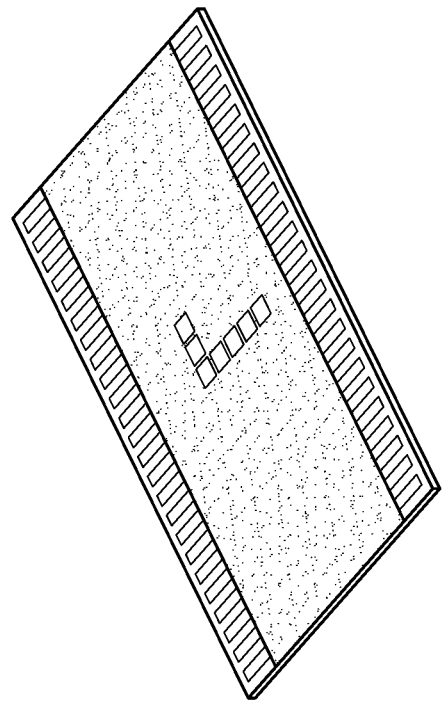
Insulate electrodes with ~5μm of dielectric
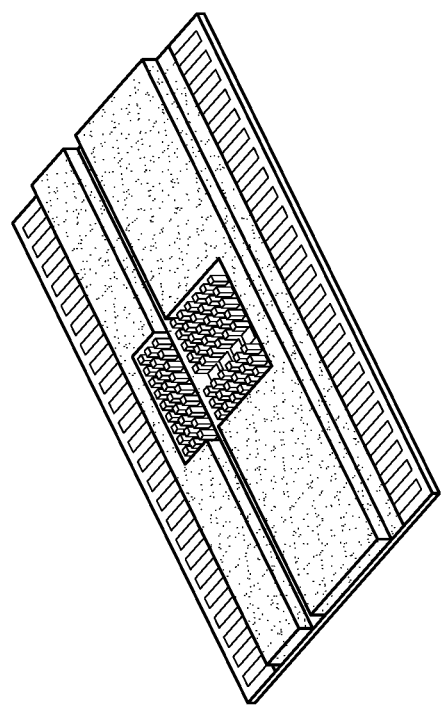
Seal channel with top layer
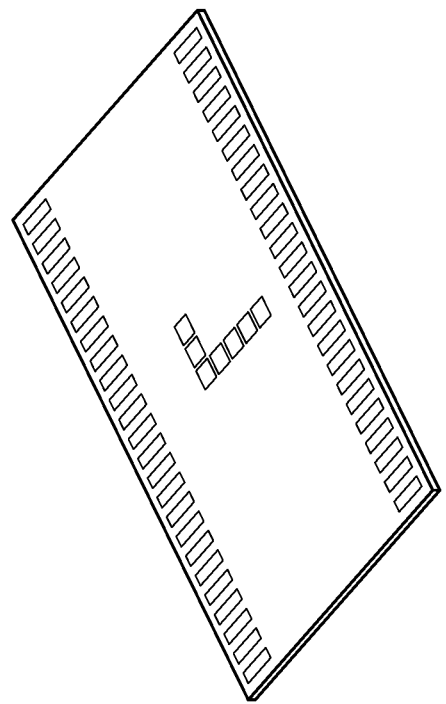
DMF electrodes plated onto a glass slide
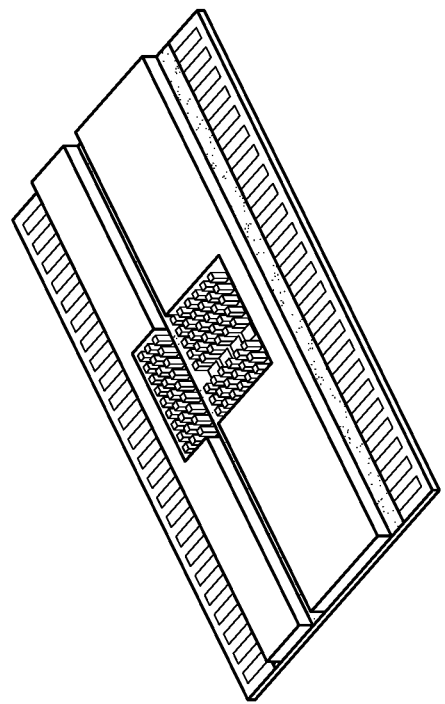
Build up channel features
FIG. 12

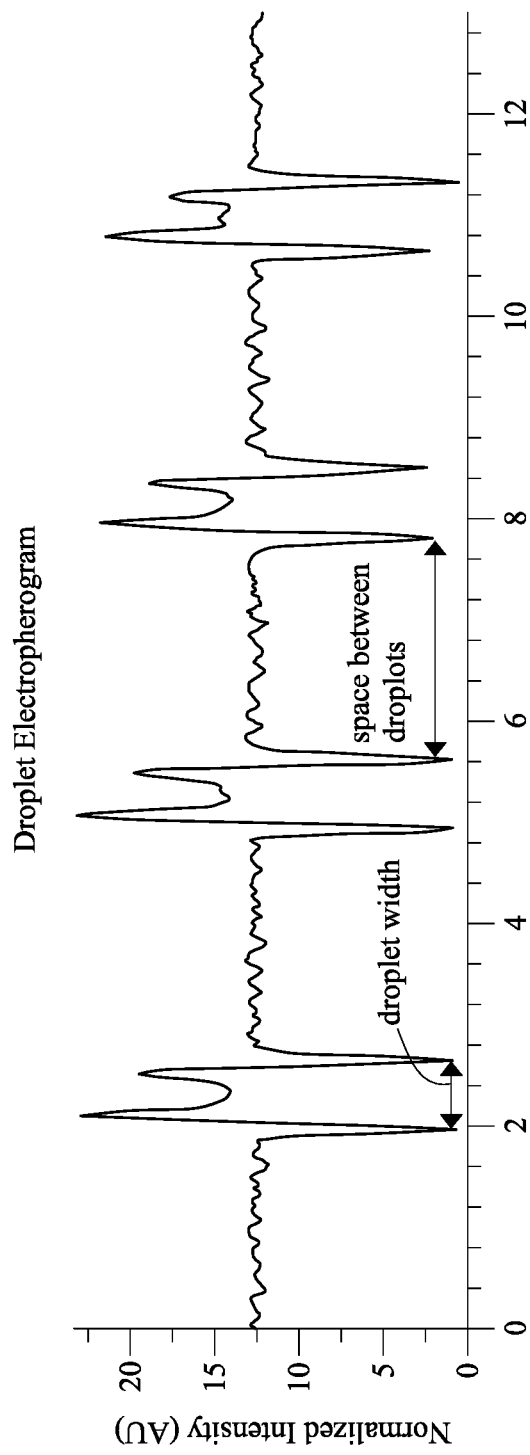
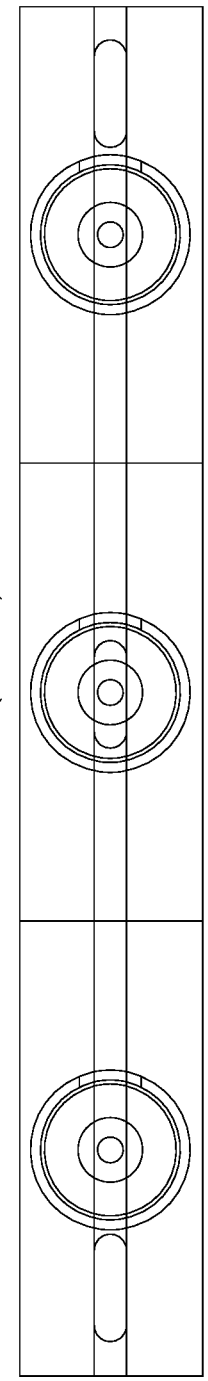
FIG. 24

METHOD AND DEVICE FOR TRACKING AND MANIPULATION OF DROPLETS

RELATED APPLICATIONS

The present application claims priority to U.S. Provisional Application No. 62/068,595, filed on Oct. 24, 2014. The content of this related application is herein expressly incorporated by reference in its entirety.

STATEMENT REGARDING FEDERALLY SPONSORED R&D

RELATED APPLICATIONS

The present application is the U.S. National Phase of International Application No. PCT/US2015/057406 entitled METHOD AND DEVICE FOR TRACKING AND MANIPULATION OF DROPLETS, filed Oct. 26, 2015 and published in the English language on Apr. 28, 2016 as WO 2016/065365, and which claims priority to U.S. Provisional Application No. 62/068,595, filed on Oct. 24, 2014. The contents of these related applications are herein expressly incorporated by reference in their entirety.

BACKGROUND

Field

The present disclosure relates generally to microfluidic devices and methods, and more particularly, to devices and methods for manipulating (for example, mixing, splitting and sorting) droplets, and those for sensing and tracking of droplets.

Description of the Related Art

In biological research, it is challenging to screen massive number of biological samples. For example, in high-throughput screening applications, the first step is often to allow for the identification of 'hits' from massive chemical libraries. Some drug discovery applications are to screen candidates on the basis of their effects on cells and organisms or target specific proteins to find rare variants with irregular activity. In order to detect the target cells or proteins, common sorting tools such as flow cytometer[1] and mass spectrometry[2] have been used to screen and sort according to their interactions and their activity with other cells and proteins.

In a conventional screening procedure, samples are typically prepared by manual intervention techniques using pipettes and tubes or large automated robotic systems to mix multiple reagents and to store these samples short- or long-term in microtiter plates. While microtiter plate-based screening is the gold standard, it suffers from many disadvantages including but not limited to: a) throughput limited to number of wells in a plate (96-~1500), b) relatively large volumes needed for screening, c) potential problem of evaporation for high density plates, d) manual pipetting for mixing reagents, e) cost of robots in case of robotic pipetting, and f) difficulty of mixing reagents in a well on high-density plates.

An alternative method to flow cytometry and mass spectrometry for mixing reagents and sorting cells and proteins and a microtiter plate for screening reactions and selecting desired reactions for further analysis is the use of microfluidics. For example, microchannels can be fabricated (for example, 10-500 μm widths and depths) and it represents a potential solution to screen and to sort cells with significant savings in volumes (pL-nL) and with significant increase in throughput. One type of microfluidics that is capable of evaluating multiple experimental conditions in parallel is droplet microfluidics.[3] Droplet microfluidics takes advantage of immiscible aqueous solutions and fluorocarbons/hydrocarbons to generate thousands of aqueous droplets per second[4] for single-cell studies,[5] enzyme kinetic assays,[6] and drug discovery applications.[7] The key advantage of droplet microfluidics is the high throughput as hundreds to thousands of droplets can be generated and processed in a very short amount of time in a credit-card sized chip. A reference reports that generating the droplets in a droplet microfluidic device can be done at kHz frequencies.[8]

There are two types of droplet microfluidic platforms—one using droplets-in-flow and the other using droplets on electrodes (also called digital microfluidics or DMF). The strength of DMF devices is the ability to finely control the movement of droplets. On the other hand, DMF has a limited capacity to control the size of the droplets generated because in DMF devices, input sample is delivered directly on an electrode as a droplet, and a combination of electrodes are then used to split the large droplet into smaller droplets. Droplets-in-flow microfluidics is able to generate droplets of substantially uniform size in high-throughput. The range of droplet size that droplet microfluidics is broad (pL-nL), a characteristic that DMF does not have.

Droplet microfluidics often requires a mixing mechanism to add reagents and a sorting mechanism to organize the individual droplets containing cells, proteins, or DNA. Current mixing mechanisms rely on passive diffusive techniques and use long serpentine channels to recirculate the flows in the droplet after adding the reagents.[9] These mixing mechanisms are not reliable methods of combing droplets containing different reagents and are severely limited in their abilities. This limitation forces solutions to be mixed in bulk before being added to the device.

Methods for droplet merging have been introduced using electro-coalescence in reduced-flow cells,[10] but these devices rely on droplets colliding at a stoichiometric ratio that is hard to maintain with flow rates alone. There are other methods available that inject droplets with reagents using a positive pressure at an oil-water interface with electro-coalescence,[11, 12] but the amount of reagent injected is difficult to control and adding more than one reagent in series becomes even more unreliable. Current sorting mechanisms use the size of the droplets,[13] gravity,[14] air pressure[15] or dielectrophoretic[8, 16] forces to direct particles into their respective channels. However, these methods are typically capable of conducting only binary sorting (i.e., sorting droplets between two channels), which can be problematic if you have a library of droplets containing more than two types of samples. Therefore, there is a need for a controlled and reliable droplet merging and sorting microfluidic technique. The present disclosure relates to droplets-in-flow and droplets-on-electrodes, and retains benefits of both platforms.

SUMMARY

The present application relates to devices and methods useful for confined-channel digital microfluidics that combine high-throughput droplet generators with digital microfluidic for droplet manipulation and an off-chip sensing system for droplet tracking.

In some embodiments, a microfluidic device comprises (a) a droplet-generating apparatus comprising one or more droplet channels, wherein the droplet-generating apparatus is configured to merge two or more immiscible fluids to generate droplets in at least one of the one or more droplet channels; and (b) a droplet control apparatus comprising a plurality of electrodes, wherein the droplet control apparatus is in fluid communication with the droplet-generating apparatus. The microfluidic device can, in some embodiments, further comprise at least one inlet channel connected to the one or more droplet channels. In some embodiments, the microfluidic device comprises at least one outlet channel in fluid connection with the flow control apparatus, the droplet control apparatus, or both. In some embodiments, the droplet control apparatus comprises one or more channels, wherein the plurality of electrodes is operably attached to the one or more channels. In some embodiments, the droplet-generating apparatus is configured to merge two immiscible fluids to generate droplets in at least one of the one or more droplet channels.

In some embodiments, the microfluidic device further comprises a flow control apparatus in fluid communication with the droplet-generating apparatus, the droplet control apparatus, or both. The flow control apparatus, in some embodiments, is configured to alter the flow rate of the droplets in the microfluidic device.

In some embodiments, the droplet-generating apparatus comprises a vacuum, a hydrodynamic flow generator, a hydrodynamic pressure generator, or any combination thereof.

In some embodiments, at least one of the two immiscible fluids is aqueous. In some embodiments, at least one of the two immiscible fluids comprises oil.

In some embodiments, the droplets generated from the droplet-generating apparatus are about 1 pL to about 1 mL in volume. In some embodiments, droplets generated from the droplet-generating apparatus are substantially uniform in size.

In some embodiments, the flow control apparatus comprises one or more valves, one or more pumps, or any combination thereof. In some embodiments, the flow control apparatus comprises one or more obstacles. In some embodiments, the obstacle is a post, a plurality of posts, a pillar, a plurality of pillars, a ramp, a bump, a droplet (for example, a droplet captured on an electrode), or a combination thereof.

In some embodiments, the flow control apparatus comprises a channel or a portion of a channel that is widening. In some embodiments, the flow control apparatus comprises a channel or a portion of a channel that is constricting.

The microfluidic device can comprise at least one inlet channel connected to the one or more droplet channels. In some embodiments, the flow control apparatus comprises at least one channel connected to at least one inlet channel. In some embodiments, the flow control apparatus comprises at least one channel connected to at least one of the one or more droplet control apparatus.

The droplet apparatus can comprise at least one or more channels, including but not limited to, one or more access channels for alternative fluidic flow, one or more side channels in which droplets can be set aside for merging, splitting or other types of droplet manipulation, or any combination thereof. In some embodiments, the droplet generation apparatus comprises at least one channel connected to at least one inlet channel. In some embodiments, the droplet generation apparatus comprises at least one channel connected to at least one of the one or more droplet control apparatus. In some embodiments, the plurality of electrodes is configured to guide the movement of droplets through the droplet control apparatus. In some embodiments, the plurality of electrodes is on the floor of one or more channels in the droplet control apparatus, on the ceiling of one or more channels in the droplet control apparatus, or any combination thereof.

In some embodiments, the microfluidic device further comprises at least one heating pad. In some embodiments, the microfluidic device further comprises an incubation apparatus. In some embodiments, the microfluidic device further comprises an additional layer of electrodes.

Some embodiments disclosed herein provide a method for manipulating droplets, comprising: (a) generating droplets by merging two or more immiscible fluids; (b) altering the flow rate of the droplets in a flow control apparatus; and (c) controlling the movement of said droplets in a droplet control apparatus comprising a plurality of electrodes, wherein the droplet control apparatus is in fluid communication with the flow control apparatus. In some embodiments, the droplets are generated by merging two immiscible fluids in step (a).

In some embodiments, the droplets are generated under a hydrodynamic flow, a hydrodynamic pressure, or any combination thereof. In some embodiments, the average volumes of said droplets are about 1 pL to about 1 mL. In some embodiments, said droplets are substantially uniform in size.

In some embodiments, controlling the movement of said droplets comprises controlling the direction of the movement of said droplets, controlling the speed of said droplets, controlling the orientation of said droplets, controlling the position of said droplets, capturing said droplets, and any combination thereof. In some embodiments, controlling the movement of the droplets comprises altering the movement of the droplets by hydrodynamic flow, the electrodes, or any combination thereof. In some embodiments, the movement of the droplets by the electrodes comprises turning the electrodes on and off.

In some embodiments, the flow control apparatus comprises a valve, a pump, an obstacle or a plurality of obstacles, a channel or a portion of a channel that is widening, narrowing or constricting, or any combination thereof.

In some embodiments, controlling the movement of the droplets comprises splitting one or more of the droplets, merging two or more of the droplets, or any combination thereof. In some embodiments, the droplets are merged and mixed by the electrodes.

In some embodiments, controlling the movement of the droplets comprises conducting binary or multiple sorting of the droplets by hydrodynamic flow, the electrodes, or any combination thereof. In some embodiments, the droplets control apparatus comprises one or more side channels containing a plurality of electrodes, wherein optionally the plurality of electrodes is used for controlled arraying of individual droplets.

In some embodiments, the droplets comprise one or more biological materials, one or more chemical material, or any combination thereof. In some embodiments, said biological material comprises a protein, a peptide, a small molecule, a lipid, a saccharide, a nucleic acid, a cell, culture media, or a combination thereof. In some embodiments, the nucleic acid is DNA, RNA, or both. In some embodiments, the protein is an enzyme. In some embodiments, the small molecule is an antibiotic. In some embodiments, the small molecule is an enzyme substrate, a co-factor, or both. In some embodiments, said cell is selected from the group consisting of a bacterial cell, a mammalian cell, an insect cell, a plant cell, an algal cell, a fungal cell, and a combination thereof.

Some embodiments disclosed herein provide a sensing device comprising: (a) a channel through which droplets flow; (b) a fiber optic cable placed next to the channel; (c) a light source to which said fiber optic is connected; and (d) a light detector to which said fiber optic is connected and which detects the partial blockage of light when said droplets pass under the light emitted from the fiber optic cable. In some embodiments, the fiber optic cable is placed under the channel through which droplets flow. In some embodiments, the fiber optic cable is placed inside the channel through which droplets flow. In some embodiments, the light detector is a photomultiplier tube, a photodiode, a charge-coupled device (CCD), or a complementary metal-oxide-semiconductor (CMOS).

A more complete understanding of the present disclosure, as well as other features and advantages of the disclosure, will be apparent from the following detailed description and the accompanying drawings.

BRIEF DESCRIPTION OF THE DRAWINGS

The foregoing aspects and others will be readily appreciated by the skilled artisan from the following description of illustrative embodiments when read in conjunction with the accompanying drawings.

As shown in FIG. 5, DMF electrodes can be used to control the movement of droplets and direct them to either of the four wells in the figure. This way, the device can select and sort each individual droplet.

FIG. 6 schematically illustrates a non-limiting embodiment of a digital microfluidic valve as described herein. In FIG. 6, a digital microfluidic valve redirects the fluid flow by controlling the movement of a valve droplet whose size is similar to the width of channel via DMF. In the top figure, the valve droplet is positioned by DMF such that it does not block an active fluid stream flowing from left to right in the figure. On the other hand, when DMF directs the valve droplet to the active fluid stream, as shown in the bottom figure of FIG. 6, the resistance in the active fluid stream increases, which allows droplet sorting and fluid redirection to a different channel which formerly had high resistance (a perpendicular channel in the figure). FIG. 6 shows that a digital microfluidic valve enables the control of microfluidic flows using DMF.

In FIG. 7, droplets containing cells are delivered into the fluid channel. The droplets are slowed down to help the DMF electrodes to capture the droplets, and then the electrodes control the movement of the droplets and direct them to the perpendicular channel. Electroporator electrodes that generate electrostatic field, external from the DMF electrodes which are coated by an insulating layer, lie across the perpendicular channel. When the droplets containing cells flow across the electroporator electrodes, the cells are subject to electrostatic field and undergo electroporation, during which their cell membranes become more permeable.

As shown in FIG. 8, target droplets containing cells and DNA flow through the inlet cooling channel whose temperature is maintained at 0° C. The speed of the droplets is slowed down, and the DMF electrodes control the movement of the droplets and redirect them to the perpendicular channel for heat shock. 42° C. heating pad and 0° C. cooling pad are placed across the perpendicular channel, and the droplets containing cells and DNA that move through the perpendicular channel become subject to the heating phase followed by the cooling phase. The heating and cooling phases enable cell transformation in which the DNA segments in the droplets are introduced to the cells. DMF allows control over heating and cooling durations for transformation of host cells, such as *E. coli*. After transformation, the droplets including transformed cells are directed by DMF electrodes to an outlet incubation channel with media whose temperature is held at 37° C.

FIG. 10 demonstrates the successful transformation of DH5α cells in the DMF device FIG. 11 show fluorescence images of LB agar plates containing *E. coli* DH5α cells following transformation with pcDNA3-Clover GFP plasmid DNA by the DMF device (A) and the conventional tube-based method (B). Fluorescence level of DH5α cells transformed using the DMF device is similar to that of DH5α cells transformed using the conventional method. Thus, FIG. 11 demonstrates that transformation efficiency of the DMF device is at least similar to that of the conventional method.

FIG. 12 shows a general designing procedure of a device described in Example 2.

FIG. 24 shows droplet tracking using a non-limiting embodiment of the off-chip sensing system according to the embodiments described herein.

DETAILED DESCRIPTION

Figure 1:
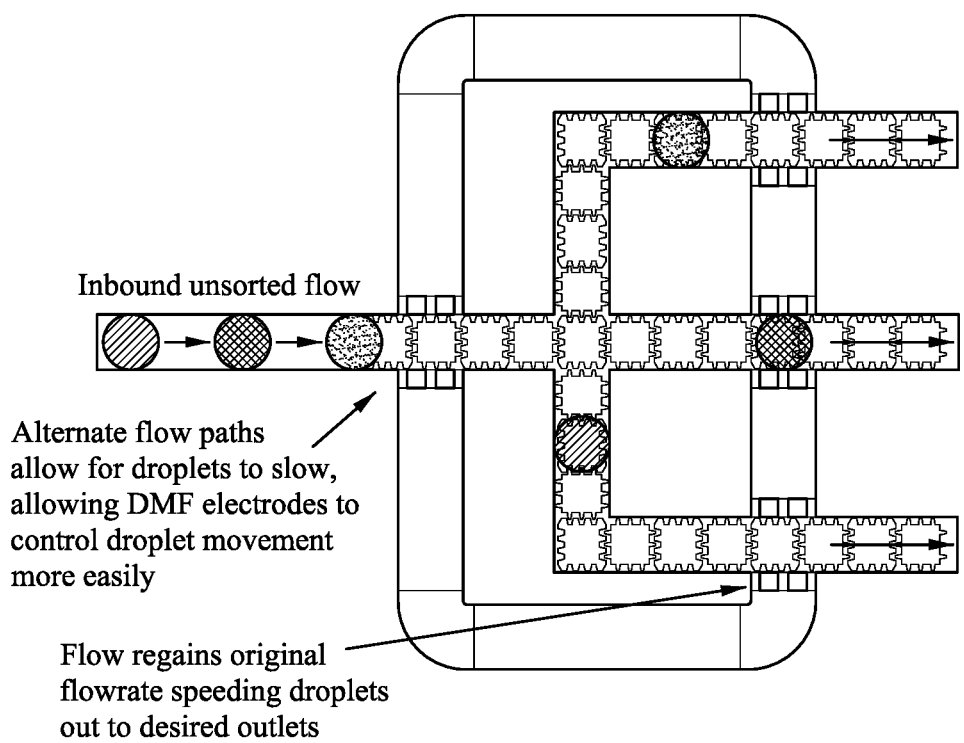
FIG. 1 shows a diagram of a 3 outlet sorting device according to the embodiments described herein. Alternate flow paths allow for droplets to slow, allowing digital-microfluidic electrodes to control the movement of the droplets more easily. DMF electrode pads direct droplets of different characteristics to various outlets.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

These and other objects, advantages, and features of the disclosure will become apparent to those persons of skill in the art upon reading the details of the disclosure as more fully described below.

The present disclosure provides for devices and methods useful for combining high-throughput droplet generators with digital microfluidic for droplet manipulation. In some embodiments, the devices and methods described herein maintains the advantages of the two paradigms of microfluidics: (1) droplet microfluidics to generate droplets and (2) digital microfluidics (where electrodes are patterned below the channel) to easily mix droplets together and to sort a library of droplets (i.e., sort more than two types of droplet species) simply by application of electric potentials, but avoid their pitfalls.

Microfluidic Methods and Devices for Manipulating Droplets

A microfluidic device for manipulating droplets is disclosed herein. In some embodiments, the device comprises: (a) a droplet-generating apparatus comprising one or more droplet channels, wherein the droplet-generating apparatus is configured to merge two immiscible fluids to generate droplets in at least one of the one or more droplet channels; (b) at least one inlet channel connected to the one or more droplet channels; (c) a droplet control apparatus comprising a plurality of electrodes in fluid communication with the flow control apparatus; and (d) at least one outlet channel in fluid connection with the flow control apparatus, the droplet control apparatus, or both.

In some embodiments, the device further comprises a flow control apparatus in fluid communication with the droplet-generating apparatus and configured to alter the flow rate of the droplets in the microfluidic device.

In some embodiments, at least one of the two immiscible fluids is aqueous. In some embodiments, at least one of the two immiscible fluids comprises hydrophobic fluid (e.g., oil). In some embodiments, droplets are generated by merging two or more immiscible fluids with one containing hydrophobic liquid (oil) and another containing hydrophilic liquid (aqueous). This provides a much higher throughput and droplets that are more uniform in size.

In some embodiments, the droplets are generated under hydrodynamic pressure and/or hydrodynamic flow. For example, the droplet-generating apparatus can comprise a vacuum, a hydrodynamic flow generator, a hydrodynamic pressure generator, or any combination thereof. Without being bound by any particular theory, it is believed that the hydrodynamic flow and/or pressure enable formation of small and substantially uniform-in-size droplets. The size of the droplets can vary. For example, the droplets generated from the droplet-generating apparatus can be about 1 pL to about 1 mL in volume. In some embodiments, the droplets can have a volume of, or about, 1 pL, 5 pL, 10 pL, 50 pL, 100 pL, 500 pL, 1 nL, 5 nL, 10 nL, 50 nL, 100 nL, 500 nL, 1 μL, 5 μL, 10 μL, 50 μL, 100 μL, 500 μL, 1 mL, or a range between any two of these values (inclusive of the starting and ending points). In some embodiments, the droplets generated from the droplet-generating apparatus are substantially similar in size. For example, about 50%, 60%, 70%, 80%, 90%, 95%, 99%, or more of the droplets can be of the same or substantially same size (±10% in difference). In some embodiments, about 50%, 60%, 70%, 80%, 90%, 95%, 99%, or more of the droplets have a volume of, or about, 1 pL, 5 pL, 10 pL, 50 pL, 100 pL, 500 pL, 1 nL, 5 nL, 10 nL, 50 nL, 100 nL, 500 nL, 1 μL, 5 μL, 10 μL, 50 μL, 100 μL, 500 μL, 1 mL, or a range between any two of these values (inclusive of the starting and ending points).

Droplets generated from the droplet-generating apparatus can contain solvent and both soluble and insoluble solutes. The term "aqueous" fluid in Claim 4 includes not only solvent but also solvent with either soluble or insoluble solutes. DNA segments in water are an example of solvent with soluble solutes. Insoluble solutes include but are not limited to cells and hydrophobic solutes. An example of these cells includes a bacterial cell (e.g., *E. coli*), a mammalian cell, an insect cell, a plant cell, an algal cell, and a fungal cell (e.g., yeast).

The flow control apparatus disclosed herein can comprise one or more valves, one or more pumps, or any combination thereof to alter the flow rate of the droplets in the microfluidic device. For example, a valve, a pump, or a combination thereof can be used to block, slow down, speed up, or allow passing of one or more droplets at certain points of the microfluidic device.

The flow control apparatus can also comprise one or more obstacles to alter the flow rate of the droplets in the microfluidic device. For example, the obstacle(s) can be used to block, slow down, speed up, or allow passing of one or more droplets at certain points of the microfluidic device. The shape, size (e.g., width, length and depth), and material of the obstacle(s) are not particularly limited. For example, the obstacle can be a post, a pillar, a ramp, a bump, or a combination thereof. The obstacle can be, for example, a triangle, with round corner, round, square, oval, a rectangle, or any combination thereof.

Figure 13:
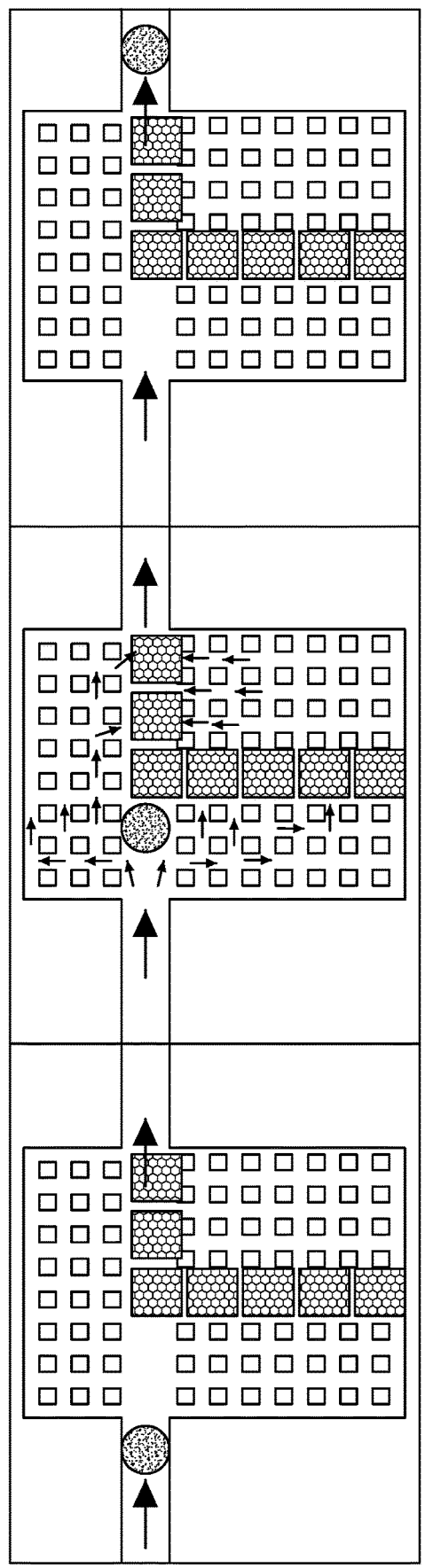
FIG. 13 schematically illustrates a mode of operation of the device described in Example 2.

The flow control apparatus can comprise a channel or a portion of a channel that is widening or constricting to alter the flow rate of the droplets. In general, the flow rate of the droplets will decrease when the droplets flow from a channel or chamber (or a portion of the channel or chamber) with smaller cross-section to a channel or chamber (or a portion of the channel or chamber) with larger cross-section, and vice versa. In some embodiments, the flow control apparatus comprises a widening channel in which the flow rate of the droplets decreases. In some embodiments, the flow control apparatus is a widening channel wherein the droplet is blocked by obstacles within the channel. In some embodiments, the flow control apparatus comprises a constricting channel in which the flow rate of the droplets increases. FIG. 13 shows a non-limiting embodiment in which pillars are used as obstacles within the microfluidic channel to alter the flow rate of the droplets. The obstacles in the widening channel may block or slow down both droplets and the fluid, or may selectively block droplets only and not the fluid.

The flow control apparatus can also comprise a channel or a portion of a channel that is constricting or widening to alter the flow rate of the droplets. In general, the flow rate of the droplets can increase when the droplets flow from a channel or chamber (or a portion of the channel or chamber) with larger cross-section to a channel or chamber (or a portion of the channel or chamber) with smaller cross-section, and vice versa. The constricting channel can be used to extract droplets from electrodes into a main channel by increasing the flow rate.

In some embodiments, the flow control apparatus comprises at least one channel connected to at least one inlet channel. In some embodiments, the flow control apparatus comprises at least one access channel connected in fluid communication with the main channel, the side channel, or the inlet channel to alter the flow rate of the aqueous droplets in an immiscible fluid (e.g., oil). In some embodiments, the flow control apparatus comprises at least one channel connected to at least one of the one or more droplet channels. In some embodiments, the flow control apparatus comprises at least one access channel connected to at least one of the one or more droplet channels to alter the flow rate of the aqueous droplets in an immiscible fluid (e.g., oil). The access channels function as alternative flow paths for a liquid and decrease the hydrodynamic pressure exerted to the droplets.

In some embodiments, the flow control apparatus is one or more side channels in fluid communication with the main channel, wherein the main channel and the side channels are connected by an aperture of a size that permits the movement of liquid, such as oil, but not the movement of the droplet through the side channels. Side channels function as alternative flow paths for a liquid and decrease the hydrodynamic pressure exerted to the droplets. In some embodiments, the flow control apparatus comprises one or more access channel in fluid communication with the main channel, the side channel, or the inlet channel in a first region in front of at least one electrode of the first plurality of electrodes, and a second region in front of at least one electrode of the first plurality of electrodes, and the access channel having aperture with a size that permits movement of a liquid (e.g., oil) and does not permit movement of the droplet through the access channel. The access channels function as alternative flow paths for a liquid and decrease the hydrodynamic pressure exerted to the droplets.

In some embodiments, the droplet generation apparatus comprises at least one channel connected to at least one inlet channel. In some embodiments, the droplet generation apparatus comprises at least one access channel connected in fluid communication with the main channel, the side channel, or the inlet channel to alter the flow rate of the aqueous droplets in an immiscible fluid (e.g., oil). In some embodiments, the droplet generation apparatus comprises at least one channel connected to at least one of the one or more droplet channels. In some embodiments, the droplet generation apparatus comprises at least one access channel connected to at least one of the one or more droplet channels to alter the flow rate of the aqueous droplets in an immiscible fluid (e.g., oil). The access channels function as alternative flow paths for a liquid and decrease the hydrodynamic pressure exerted to the droplets.

As disclosed herein, in order to address these mixing and sorting issues, in some embodiments, the droplet microfluidic platform can be integrated with another microfluidic paradigm: digital microfluidics (DMF)[17]. In DMF, discrete droplets are manipulated by applying electrical fields to an array of electrode in the presence of air[18] or oil[19]. By application of a sequence of electric potential to adjacent electrodes, a droplet of fluid can be easily merged with other droplets. In addition, these droplets can be addressed individually since the droplet is isolated from its surroundings, instead of being embedded in a stream of fluid. Therefore, multistep methods involving many different reagents (e.g. cell-based assays,[20-22] clinical analysis[23, 24]) can be easily programmed. Accordingly, provided herein in some embodiments are devices and methods that combine the two paradigms of microfluidics: (1) droplet microfluidics to generate droplets and (2) digital microfluidics (DMF) to mix droplets and to sort a library of droplets.

The microfluidic device described herein can comprise a droplet control apparatus comprising a plurality of electrodes that is in fluid communication with the flow control apparatus. The electrodes can, for example, guide the movement of the droplets through the droplet control apparatus. The flow control apparatus can be in direct or indirect fluidic connection with the droplet control apparatus. In some embodiments, the droplets that have been altered flow rate by the flow control apparatus can flow into the droplet control apparatus for further manipulation. The droplets can be manipulated in various ways. For example, the flow rate of the droplets can be altered, and/or the orientation and/or the position of the droplets can also be altered. DMF electrodes can be used, in some embodiments, to temporarily capture the droplets from the bulk flow and perform functions such as merger, sorting, arraying and splitting. Droplets can then be moved off the electrodes and be reintroduced into a bulk flow of the hydrophobic liquid. In some embodiments, two or more droplets can be manipulated to merge into one droplet. In some embodiments, one droplet can be manipulated to split into two or more droplets. In some embodiments, two or more droplets can be manipulated to merge into one or more bigger droplets.

In some embodiments, each electrode in a plurality of electrodes is adjacent to at least one other electrode within the plurality of electrodes. In some embodiments, the first plurality of electrodes is optionally one electrode, and/or the second plurality of electrodes is optionally one electrode. In some embodiments, the first plurality of electrodes comprises two, three, four or five electrodes. In some embodiments, the second plurality of electrodes comprises two, three, four, or five electrodes.

The electrodes of the device, in some embodiments, are configured for use as DMF electrodes. In some embodiments, the device uses electrodes not only for manipulation of droplets, but also for other purposes. In some embodiments, some electrodes can be used for detection of droplets by measuring conductivity change in channels. Because of the conductivity difference between droplet liquid and channel liquid, overall conductivity of a channel changes when a droplet pass across the electrode. Thus, detector electrodes can be placed next to the channel to detect movement of the droplets.

In some embodiments, the droplet control apparatus can also comprise a flow control apparatus. As described above, the flow control apparatus can comprise various elements to alter the flow rate of the droplets, including but not limited to, one or more vacuum, one or more hydrodynamic flow generator, one or more hydrodynamic pressure generator, one or more obstacles, one or more widening channels (or one or more portion of a channel), access channels, and any combination thereof. In some embodiments, the droplet control apparatus functions under a hydrodynamic flow, a hydrodynamic pressure, or a combination thereof. In some embodiments, the flow control apparatus and the droplet control apparatus work simultaneously or alternatively to manipulate the movement of droplets, and not just in a sequential manner.

Types of samples suitable for use in the microfluidic device described herein can vary. For example, the sample can be a biological sample. In some embodiments, the droplets comprise water with a biological sample (including but not limited to, proteins, small molecules, lipids, saccharides, nucleic acids, cells, culture media, or any combination thereof). The microfluidic device can further comprise one or more apparatus for sample manipulation. For example, the microfluidic device can comprise at least one heating pad, an incubation apparatus for incubating the sample, electrodes suitable for performing electroporation of biological samples (e.g., cells), or any combination thereof.

Figure 7:
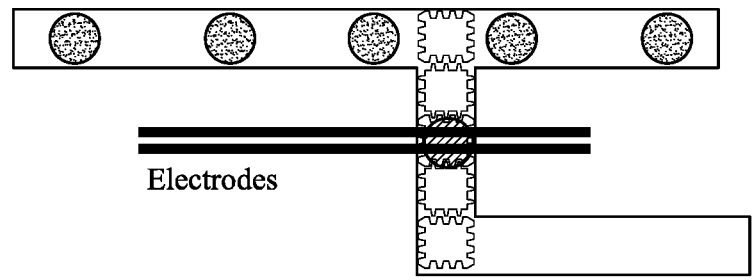
FIG. 7 schematically illustrates a non-limiting embodiment of DMF controlled cell electroporation.

In some embodiments, the device is configured for DMF controlled cell electroporation for transfection (FIG. 7). More specifically, the device comprises an additional layer of electrodes used for cell electroporation that are separate from DMF electrodes used for manipulation of droplets. DMF electrodes direct droplets from the main channel to a perpendicular channel (FIG. 7). The electroporator electrodes are placed across the perpendicular channel such that droplets and cells therein become subject to an electric field generated from the electroporator electrodes (FIG. 7). Target droplets can be redirected by DMF to electrodes to allow electroporation of cells. The movement control of droplets by DMF allows control over the electroporation duration. By merging and mixing many different combinations of DNA and cells and then conducting DMF controlled cell electroporation, the device is able to conduct high-throughput cell transfection.

Figure 17:
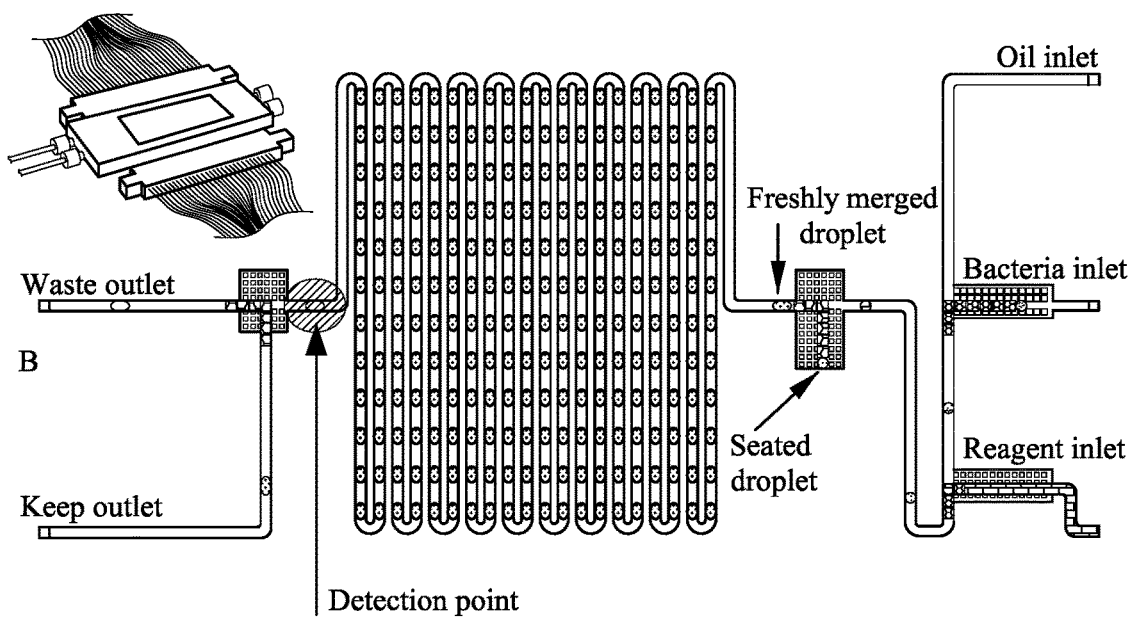
FIG. 17 shows a directed evolution of an ionic liquid (IL) tolerance. Panel A of FIG. 17 shows a photo of the actual chip. Inset A of FIG. 17 shows the schematic of the architecture and the function of the chip used for the directed evolution of IL tolerance.

In some embodiments, one of the channels can serve as an incubation channel for short-term or long-term culture of cells. For example, a serpentine channel whose temperature is held at 65° C. can serve as an incubation channel (FIG. 17). Incubated cells can be either collected or reintroduced into the flow stream.

Figure 8:
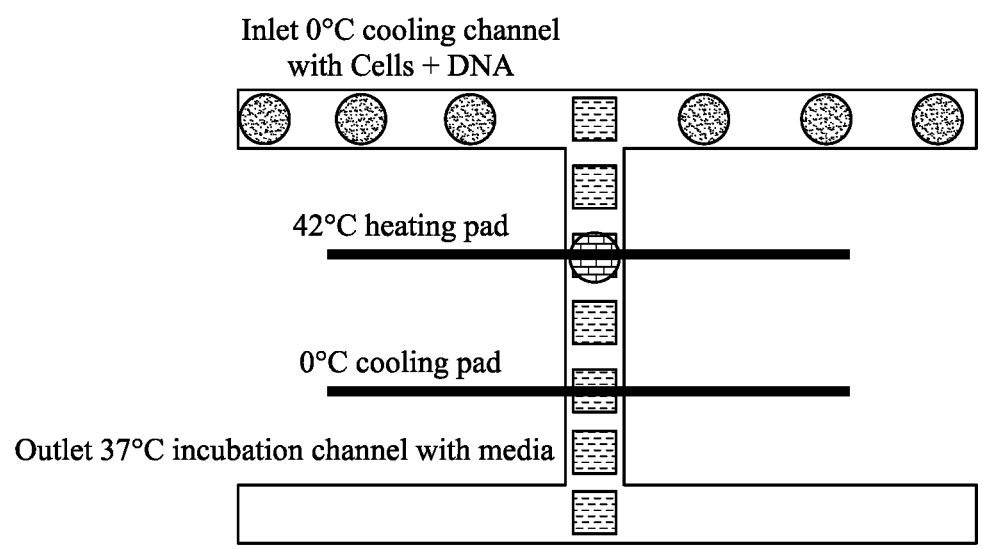
FIG. 8 schematically illustrates a non-limiting embodiment of DMF controlled cell heat shock.
Figure 9:
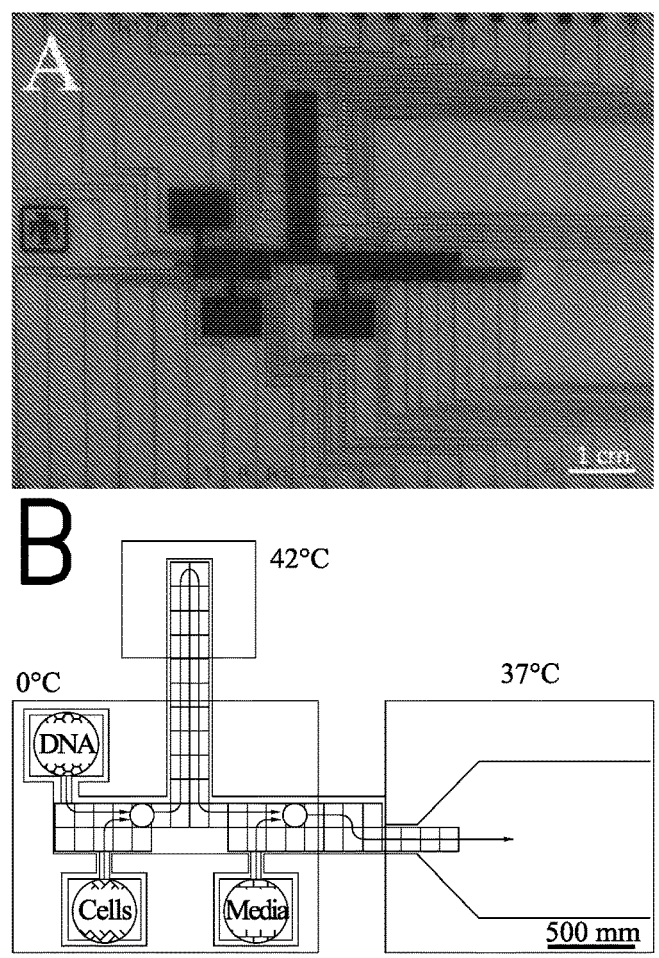
FIG. 9 show a photograph (A) and schematic illustration (B) of a DMF device for cell transformation. Arrows in panel B of FIG. 9 show the movement of droplets along the channels with different temperatures (0° C. at the inlet channels, 42° C. at the heat shock region of the main channel and 37° C. after mixing media and transformed cells). DNA and cells are mixed at 0° C. and enter the heat shock region at 42° C. Transformed cells are mixed with media at 0° C., and then incubated at 37° C.

In some embodiments, the device is configured for DMF controlled cell heat shock (FIG. 8). For example, the device comprises at least one heating pad or cooling pad. The heating pad and the cooling pad can exist as an electrode across a channel or channels so that droplets flowing across the heating or cooling electrode are subject to heating or cooling, respectively. Alternatively, the heating pad and the cooling pad can exist as pads on top of or under multiple channels to hold the covered area at certain temperature. In FIG. 9, three temperature pads maintain different regions of the device at 0° C., 37° C. and 42° C., respectively. Target droplets can be redirected by DMF to electrodes for heat shock. DMF allows control over heating and cooling durations for transformation of a host cell, such as *E. coli*.

In some embodiment according to the present disclosure, a device comprises a microfluidic channel, comprising: (a) a floor, (b) a main channel, (c) a side channel, (d) a first plurality of electrodes on the floor of the main channel such that a droplet can be moved from one electrode to an adjacent electrode in the first plurality of electrodes, (e) a means to prevent the droplet from moving due to hydrodynamic pressure applied to both ends of the droplet in the main channel, and (f) a second plurality of electrodes on the floor of the side channel. In some embodiments, when the device is in operation, a hydrodynamic pressure can be used to move a droplet in the main channel but not in the side channel. In some embodiments, when the device is in operation, the hydrodynamic pressure is also applied to the side channel. The device allows for the droplet to 1) move to the first plurality of electrodes by hydrodynamic pressure and then 2) move to any of the electrodes in the first or second pluralities of the electrodes by passing the droplet from one electrode to an adjacent electrode under the dielectrophoretic force generated by the electrodes, while the hydrodynamic pressure is continuously applied. Using the device, while under continuous hydrodynamic pressure, a droplet from a series of droplets can be selectively set aside from the series, or the droplet can be shunted off to the side channel to a completely direction different from the main channel.

The device is configured such that the device can move the droplet by applying hydrodynamic pressure on both ends of the droplet so that the droplet moves in the direction of the end that has a lower hydrodynamic pressure, except the droplet cannot be moved by applying hydrodynamic pressure on at least one electrode of the first plurality of electrodes due to the means of (e). In some embodiments, the droplet cannot be moved by applying hydrodynamic pressure on every electrode of the first plurality of electrodes. In some embodiments, the droplet cannot be moved by applying hydrodynamic pressure on every electrode of the first plurality of electrodes, except for one electrode the first plurality of electrodes.

Some embodiments provides a method for implementing mixing and sorting of droplets inside microfluidic channels. In some embodiments, this method is based on amalgamating two types of microfluidic devices: (1) droplet microfluidics for high-throughput droplet generation and (2) digital microfluidic (DMF) for the concise control of droplet manipulation. The basis of the device uses electrodes placed in channels that confine the droplets to a path along the DMF electrodes, allowing movement of droplets within each channel. Using this method, our devices can reliably merge droplets of different reagents of a controlled volume, and sort droplets into many different outlets.

In some embodiments, the device comprises one or more of the following aspects: (1) a first hybrid system between droplet and digital microfluidics, (2) a first microfluidic system (of any format) capable of sorting multiple species (not simply binary sorting), and (3) a first microfluidic system that integrates micron-sized electrodes below the channel to merge and to sort droplets.

Figure 3:
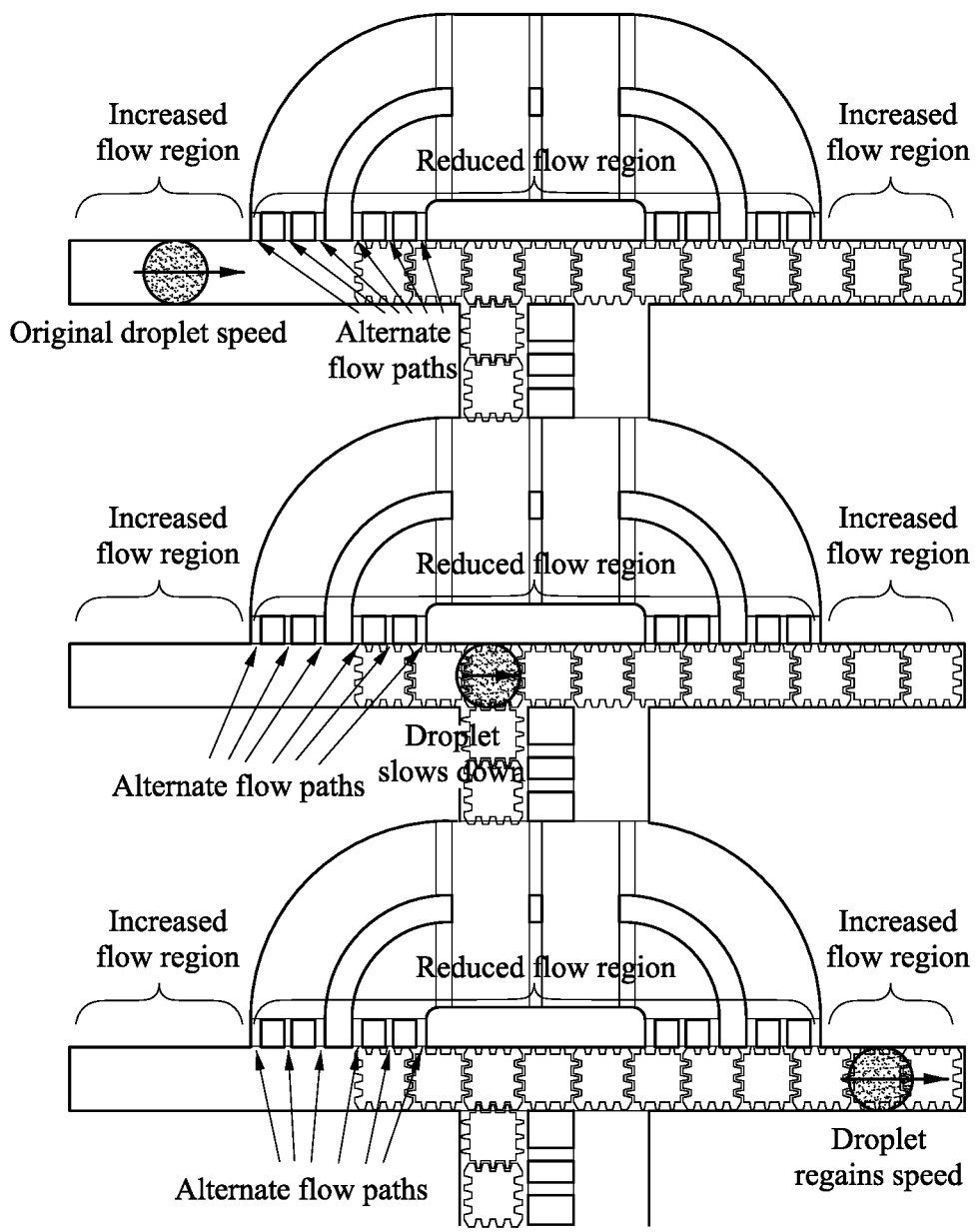
FIG. 3 schematically illustrates the functionality of alternate flow paths present in both the sorting and merging devices. These alternate flow paths enable the droplet to experience a lower hydrodynamic force, allowing easier manipulation by the dielectrophoretic force exerted by the DMF electrodes. When the droplets reach the region where alternate flow paths start, the droplets begin to slow down before reaching DMF electrodes. The reduced speed of the droplets makes them more amenable to electrowetting by DMF electrodes. By turning on and off different sets of DMF electrodes, the device can control the movement of the droplets and direct them either to the horizontal outlet or the lower cavity shown in the figure. Once the droplets are moved to the horizontal outlet where the alternate flow paths re-converge, the droplet experiences the full original hydrodynamic force and flows down the channel at its original speed.
Figure 4:
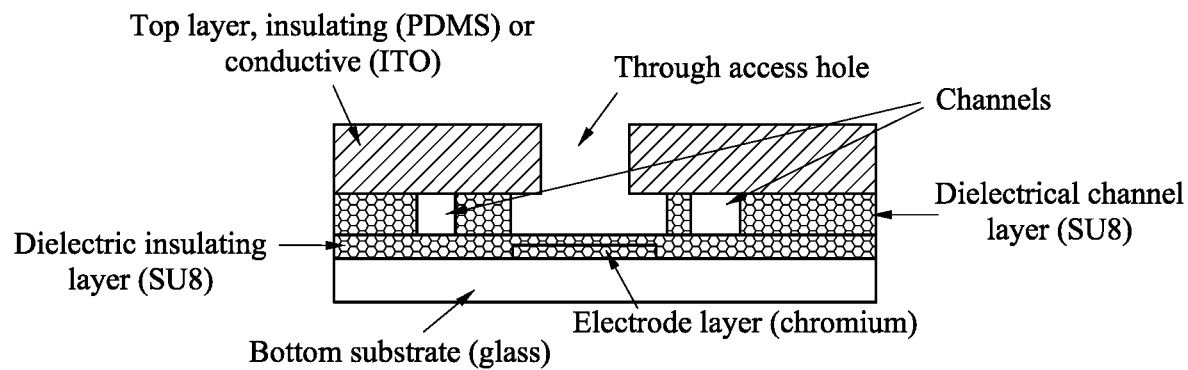
FIG. 4 schematically illustrates the side view of a non-limiting embodiment of the microfluidic device described herein. Different layers in the device are shown in FIG. 4. The materials for each of the layers can vary. In some embodiments, the basic design uses a structural bottom substrate, layered with electrodes insulated by a dielectric material, with a channel layer oriented over the electrodes, and finally a top sealing layer with through holes. The top sealing layer can be conductive, in which case the top layer serves as a ground, or insulating, in which case a ground must be included in the electrode layer.

In some embodiments, the device or method comprises a novel aqueous droplet sorting ability and droplet merging. Both devices rely on droplets mass produced in a classical droplet microfluidic function, which are placed into a channel made reservoir, which are then forced at a controlled rate by an automated pressure system into a channel that will intersect the merger and/or sorter. Once an aqueous droplet encounters a merger/sorter its speed is reduced by alternate flow paths (middle panel of FIG. 3). This allows for the DMF electrodes to exert a dielectrophoretic force on the droplets without combating a strong hydrodynamic force. The DMF electrodes move a droplet from electrode to electrode, eventually moving the droplet to the outlet where the aforementioned alternate flow paths re-converge (Bottom panel of FIG. 3). At this point the hydrodynamic force of the high flow rate forces the droplet out at the original flow rate.

The sorting device allows for droplets discernable by size, fluorescent wavelength or other characteristic to be sorted into one of several channels. The number of sortable outlets can be expanded to any number, with higher order sorters requiring auxiliary inlet flow channels to maintain flow at the outlets. Inbound unsorted droplets enter the DMF electrode region, where alternate flow paths slow the droplets. A photomultiplier tube (PMT) records the wavelength and intensity of the droplet's absorbance or fluorescence (or other detector/metric), and sends a signal to the DMF controller, directing it to one of several channels. Once the droplet reaches the outlet, the alternate flow paths re-converge, speeding the droplets out to their respective outlets (FIG. 1).

Figure 2:
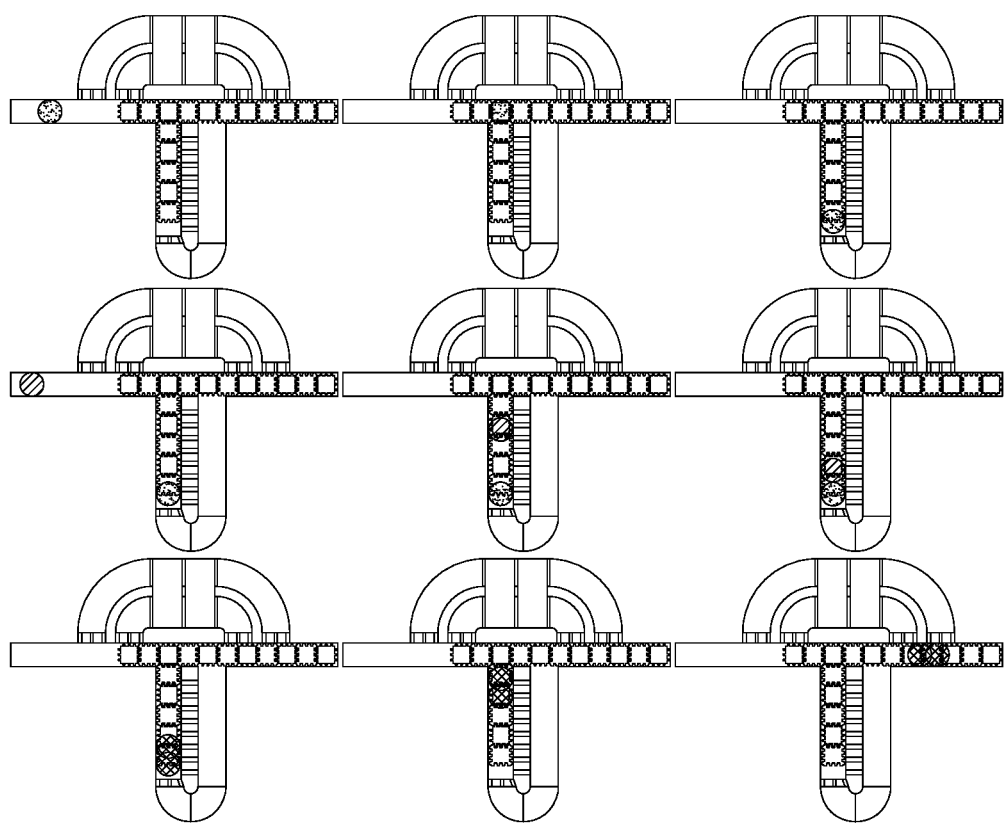
FIG. 2 schematically illustrates a sequence of merging two droplets in a device according to the embodiments described herein. Selected droplets are moved via DMF electrode pads into the lower cavity, where they are then merged. Once merged, the droplets are moved out of the cavity to the horizontal outlet.

The merging device allows for multiple droplets to be merged together in a dependable and controlled manner. As the first droplet approaches (top-left panel of FIG. 2), a controller detects its presence using a capacitive measurement, directing the droplet via DMF electrodes into the bottom of the cavity (top-center and top-right panels of FIG. 2). The $2^{nd}$ droplet approaches and is also directed into the bottom of the cavity (middle-left and middle-center panels of FIG. 2), merging the two droplets (middle-right and bottom-left panels of FIG. 2). The merged droplet (black) is then moved directed to the outlet to its next destination (bottom-center and bottom-right panels of FIG. 2). The number of different reagent containing droplets merged is limited only by the depth of the merging cavity. Droplet mergers can be linked in series to allow for virtually infinite number of reagent combination.

Figure 5:
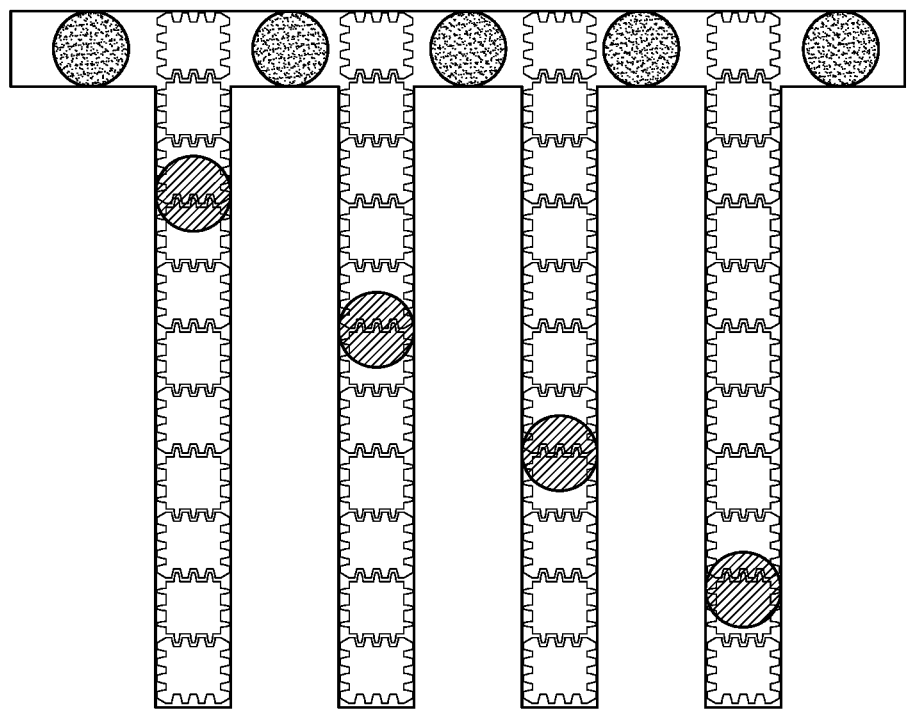
FIG. 5 schematically illustrates a non-limiting embodiment of controlled arraying of individual droplets as describe herein.

In some embodiments, the device is configured for controlled arraying of individual droplets (FIG. 5). Droplets can be picked from microfluidic channels and directed into wells by DMF. DMF provides controlled selection of droplets. DMF allows incubation of individually arrayed droplets for designated time span and prolonged imaging exposures In some embodiments, the device is configured to comprise a digital microfluidic valve (FIG. 6). The digital microfluidic valve is configured to move a droplet by DMF to an active fluid stream increases the resistance and allows droplet sorting/fluid redirection to formally high resistance channel.

Also disclosed herein are methods for manipulating droplets. In some embodiments, the method comprises: (a) generating droplets by merging two immiscible fluids; (b) altering the flow rate of the droplets in a flow control apparatus; and (c) controlling the movement of said droplets in a droplet control apparatus comprising a plurality of electrodes in fluid communication with the flow control apparatus. In some embodiments, the droplets are generated under a hydrodynamic flow. As describe herein, the size of the droplets can vary. In some embodiments, the average volumes of said droplets are about 1 pL to about 1 mL. In some embodiments, the droplets are substantially uniform in size as described above.

In some embodiments, controlling the movement of said droplets comprises controlling the direction of the movement of said droplets, controlling the speed of said droplets, controlling the orientation of said droplets, and any combination thereof. In some embodiments, controlling the movement of the droplets comprises altering the movement of the droplets by hydrodynamic flow, the electrodes, or any combination thereof. In some embodiments, controlling the movement of the droplets by the electrodes comprises turning the electrodes on and off. In some embodiments, controlling the movement of the droplets comprises splitting one or more of the droplets, merging two or more of the droplets, or any combination thereof. In some embodiments, the droplets are merged and mixed by the electrodes.

In some embodiments, controlling the movement of the droplets comprises conducting binary or multiple sorting of the droplets by hydrodynamic flow, the electrodes, or any combination thereof. FIG. 1 demonstrates a non-limiting example of the multiple sorting of droplets as described above.

In some embodiments, the flow control apparatus comprises a valve, a pump, an obstacle, a channel or a portion of a channel that is widening, or any combination thereof.

In some embodiments, the droplets comprise a biological material. Non-limiting examples of biological material include: proteins, small molecules, lipids, saccharides, nucleic acids, cells, culture media, or any combination thereof. In some embodiments, the droplet comprises one or more of an enzyme and a substrate for the enzyme. In some embodiments, the small molecule is an antibiotic. In some embodiments, the droplet comprises a bacterial cell, a mammalian cell, an insect cell, a plant cell, an algal cell, a fungal cell, or any combination thereof.

Figure 21:
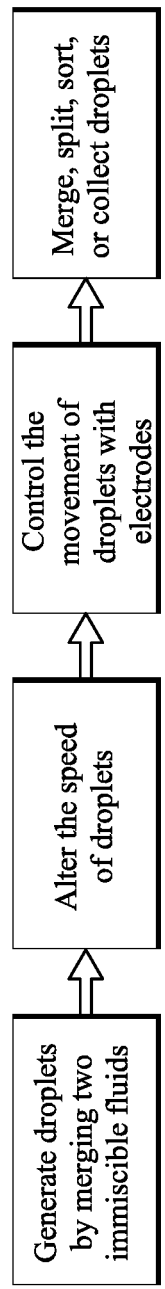
FIG. 21 is a flow chart for a non-limiting example of a method of generating, manipulating and sorting droplets.

FIG. 21 shows a flow chart for a non-limiting example of a method of generating, manipulating and sorting droplets. Droplets are generated by merging two immiscible fluids, and then droplets flow through a channel to reach a droplet control apparatus. Before droplets reach the droplet control apparatus, the hydrodynamic pressure exerted to the droplets is reduced by a flow control apparatus so that DMF electrodes associated with the droplet control apparatus can capture droplets more easily. Then, the movement of the droplets is manipulated by the DMF electrodes, which includes but is not limited to merging, splitting, and sorting.

The methods and devices described herein can be suitable for use in a method for directed evolution screening of enzyme and IL tolerance. The methods and device can also be applicable for other projects requiring a highly-controlled yet high-throughput platform, such as gene design and protein pathway engineering.

Sensing and Tracking Droplets in Droplet Microfluidics

Another important feature of droplet microfluidics is the function of sensing and tracking droplets during various manipulation/processing steps from the beginning to the end. Tracking of droplets is important not only for keeping track but also for implementing feedback/trigger for performing specific functions with selected droplets. For example, droplet tracking allows for coordination of droplets with the actuation of on-chip mechanisms such as valves or DMF electrodes. In addition, droplet tracking allows for "droplet accounting," which means keeping track of what each droplet is, and where it has been in the chip.

Techniques have been developed for live droplet tracking on-chip. For example, Elbuken et al. used a capacitive sensing method, where the change in capacitance is detected when a droplet spans two or more electrodes.[25] Nguyen et al. implemented a fiber optic detection system, where two channels were designed into the chip, one on each side perpendicular to the flow of the droplets.[26] When a droplet passes, the light generated from one fiber optic is diffracted, changing the amount of light detected in the corresponding fiber optic collecting light. Both of these methods are successful in generating a signal well above noise indicating when a droplet is present. However, the main drawback to these methods and others like them is that it requires the sensor to be designed into the chip. This has a few drawbacks: 1) sensor cannot be moved to another position without redesigning and fabrication of a new device; 2) The sensors are built in an area that is usually reserved for channel topology or actuation electrodes (in the case of DMF). This complicates and limits the design of a droplet microfluidic device. Failure of sensing elements makes the entire chip useless.

The present disclosure provides a sensing system for droplet tracking, including an off-chip sensing system. Some embodiments provide a sensing device, where the sensing device comprises: (a) a channel through which droplets flow; (b) a fiber optic cable placed next to the channel; (c) a light source to which said fiber optic is connected; and (d) a light detector to which said fiber optic is connected and which detects the partial blockage of light when said droplets pass under the light emitted from the fiber optic cable.

In some embodiments, the fiber optic cable is placed under the channel through which droplets flow. In some embodiments, the light detector is a photomultiplier tube.

In some embodiments, the off-chip sensing system can comprise a specialized fiber optic positioning manifold to aid in droplet tracking. The manifold is placed directly under the channel where the droplets will be passing. A vacuum seal is used to hold the manifold in place making relocation and exact positioning of the fiber simple and fast. Without being bound by any particular theory, it is believed that such a design allows for versatile droplet tracking at multiple locations on the device without redesigning or fabrication of a new chip, offering no obstruction to chip design. In some embodiments, the sensor relies on a fiber optic cable connected to a PMT to detect the partial blockage of light when a droplet passes under the light source. This signal can be used to determine the presence of a droplet, the length of the droplet, and flow rate depending on where the fiber optic is placed. Some non-limiting advantages of the sensor describe herein are: 1) the sensor allows a simple, inexpensive light-absorption based detection of droplets; 2) the sensor is off-chip, making the overall operation simple and user-friendly; 3) no modification of chip is required in order to use the sensor, and the same sensor is compatible with any chip architecture; 4) multiple sensors can be used with one chip, or the same sensor can be moved around to different locations on the same chip; and 5) in addition to detecting a droplet, the sensor can also measure its volume and size, which is a useful feature to detect events such as merging of droplets to form a larger droplet or splitting of a droplet into smaller ones.

Methods for making and using DMF are described, for example, in U.S. Pat. No. 8,367,370, US2007/0148763, and WO 2007/120241 (herein incorporated by reference in regards to the making and using of standard DMF elements).

REFERENCES CITED

1. G. Boeck, International Review of Cytology—a Survey of Cell Biology, 2001, 204, 239-298.
2. R. Aebersold and M. Mann, *Nature,* 2003, 422, 198-207.
3. S. Y. Teh, R. Lin, L. H. Hung and A. P. Lee, *Lab Chip.* 2008, 8, 198-220.
4. A. R. Abate, M. B. Romanowsky, J. J. Agresti and D. A. Weitz. *App. Phys. Lett.,* 2009, 94, 023503-023501.
5. E. Brouzes, M. Medkova. N. Savenelli, D. Marran, M. Twardowski, J. B. Hutchison, J. M. Rothberg, D. R. Link, N. Perrimon and M. L. Samuels, *Proceedings of the National Academy of Sciences of the United States of America,* 2009, 106, 14195-14200.

6. J. U. Shim, L. F. Olguin, G. Whyte, D. Scott, A. Babtie, C. Abell, W. T. Huck and F. Hollfelder, *J Am Chem Soc*, 2009, 131, 15251-15256.
7. J. Q. Boedicker, L. Li, T. R. Kline and R. F. Ismagilov, *Lab Chip*, 2008, 8, 1265-1272.
8. L. Mazutis, J. Gilbert, W. L. Ung, D. A. Weitz, A. D. Griffiths and J. A. Heyman, *Nat Protoc*, 2013, 8, 870-891.
9. H. Song. D. L. Chen and R. F. Ismagilov, *Angew Chem Int Ed Engl*, 2006, 45, 7336-7356.
10. K. Ahn, J. Agresti, H. Chong, M. Marquez and D. A. Weitz, *Appl Phys Lett*, 2006, 88.
11. A. R. Abate, T. Hung, P. Mary, J. J. Agresti and D. A. Weitz, *Proceedings of the National Academy of Sciences of the United States of America*, 2010, 107, 19163-19166.
12. B. O'donovan, D. J. Eastburn and A. R. Abate, *Lab on a Chip*, 2012, 12, 4029-4032.
13. Y. C. Tan, J. S. Fisher, A. I. Lee, V. Cristini and A. P. Lee, *Lab Chip*, 2004, 4, 292-298.
14. D. Huh, J. H. Bahng, Y. Ling, H. H. Wei, O. D. Kripfgans, J. B. Fowlkes, J. B. Grotberg and S. Takayama, *Anal Chem*, 2007, 79, 1369-1376.
15. X. Niu, M. Zhang, S. Peng, W. Wen and P. Sheng, *Biomicrofluidics*, 2007, 1, 44101.
16. B. Ahn, K. Lee, R. Panchapakesan and K. W. Oh, *Biomicrofluidics*, 2011, 5, 24113.
17. M. J. Jebrail and A. R. Wheeler, *Curr Opin Chem Biol*, 2010, 14, 574-581.
18. A. R. Wheeler, *Science*, 2008, 322, 539-540.
19. R. B. Fair, *Microfluid. Nanofluid.*, 2007, 3, 245-281.
20. S. C. Shih, I. Barbulovic-Nad, X. Yang, R. Fobel and A. R. Wheeler, *Biosens Bioelectron*, 2013, 42, 314-320.
21. I. Barbulovic-Nad, S. H. Au and A. R. Wheeler, *Lab on a Chip*, 2010, 10, 1536-1542.
22. I. Barbulovic-Nad, H. Yang, P. S. Park and A. R. Wheeler, *Lab on a Chip*, 2008, 8, 519-526.
23. N. A. Mousa, M. J. Jebrail, H. Yang, M. Abdelgawad, P. Metalnikov, J. Chen, A. R. Wheeler and R. F. Casper, *Sci Transl Med*, 2009, 1, 1ra2.
24. S. C. C. Shih, H. Yang, M. J. Jebrail, R. Fobel, N. McIntosh, O. Y. Al-Dirbashi, P. Chakraborty and A. R. Wheeler, *Analytical Chemistry*, 2012, 84, 3731-3738.
25. C. Elbuken, T. Glawdel, D. Chan and C. L. Ren, *Sensors and Actuators, A: Physical*, 2011, 171(2). 55-62.
26. N. T. Nguyen, S. Lassemono and F. A. Chollet, *Sensors and Actuators, B: Chemical*, 2006, 117, 431-436.

EXAMPLES

Some aspects of the embodiments discussed above are disclosed in further detail in the following examples, which are not in any way intended to limit the scope of the present disclosure.

Example 1

An Integrated Digital Microfluidic Platform for Transformation, Culture and Expression Synthetic biology experiments require optimization of pathways consisting of many genes and other genetic elements and given the large number of alternatives available for each element, optimization of a pathway can require large number of experiments consuming prohibitively-expensive amounts of DNA and enzymes. Digital microfluidics (DMF), because of its ability to process small volumes, presents a cost-effective solution for conducting high-throughput cloning and expression experiments. Herein describes a DMF device for automating all critical steps of transformation and culture including plasmid addition, transformation by heat-shock, addition of selection medium, and culture and expression of GFP.

Transformation of exogenous DNA into bacterial cells is a powerful technique for genetics studies. Microfluidic devices have routinely been employed to generate equal to enhanced transformation efficiencies with much lower reagent volumes, compared to bulk methods. K. Nagamine, S. Onodera, Y. S. Torisawa, T. Yasukawa, H. Shiku, and T. Matsue, "On-chip transformation of bacteria," *Anal Chem*, vol. 77, pp. 4278-81, July 2005; J. Sha, Y. Wang, J. Wang, L. Ren, Q. Tu, W. Liu, et al., "Capillary-composited microfluidic device for heat shock transformation of *Escherichia coli*," *J Biosci Bioeng*, vol. 112, pp. 373-8, October 2011. Unfortunately, only the gene introduction step is consistently executed on the device leaving other key procedures performed off-chip, including: DNA addition to cells, incubation, post-transformation addition of selection antibiotics, culture and analysis. Au and coworkers demonstrated a DMF platform could transform bacteria with a fluorescent gene. (S. H. Au, S. C. Shih, and A. R. Wheeler, "Integrated microbioreactor for culture and analysis of bacteria, algae and yeast," *Biomed Microdevices*, vol. 13. pp. 41-50, February 2011). However, this device did not possess integrated thermal elements; necessitating physical transfer of the device between a hot plate, ice bath and incubator and then moving the droplets to agar plates for culture.

Figure 10:
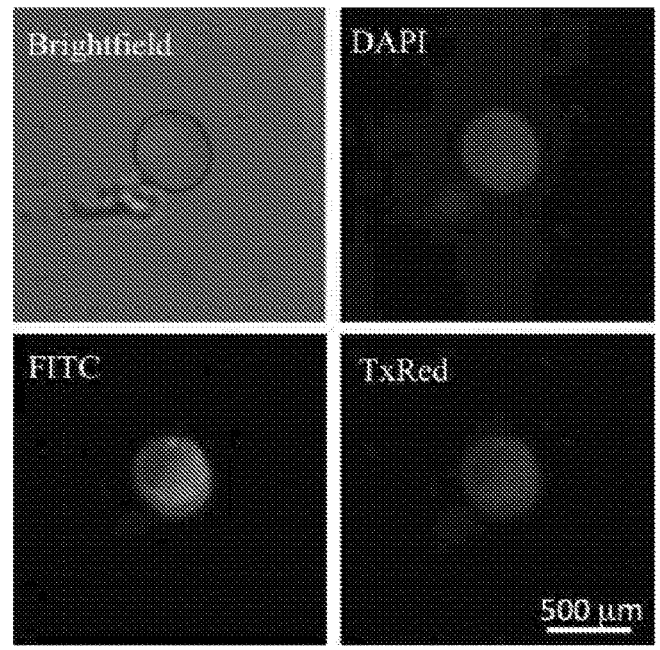
FIG. 10 is bright field and fluorescence images of a droplet containing *E. coli* DH5α cells following transformation with pcDNA3-Clover GFP plasmid DNA in the DMF device. The transformed DH5α cells exhibit brightness under the FITC filter and not under other filters, which means that the transformed DH5α cells emit green fluorescence.

Herein describes a highly integrated device based on digital microfluidics and strategically positioned peltiers that allow all transformation procedures to be carried out on a single device (panel A of FIG. 9). Three peltiers were positioned below the device to provide the 0° C., 37° C. and 42° C. temperatures employed during chemical heat-shock (panel B of FIG. 9). A 0.3 µL droplet composed of 100 chemically competent DH5α cells was initially mixed with 0.3 µL pcDNA3-Clover GFP plasmid DNA (2 ng/µL) at 0° C. for 30 s then moved to a 42° C. region of the chip for 45 s. After heat-shock the transformed cells were merged with another 0.3 µL droplet composed of Lysogeny broth (LB) and 100 µg/mL ampicillin and moved to a 37° C. incubation chamber. Following 8 hrs culture, all droplets possessed viable DH5α cells expressing GFP (FIG. 10). Transformation efficiencies were assessed by transferring the droplets immediately following heat-shock on the DMF device to an agar plate with 100 µg/mL ampicillin. Using the above experimental conditions, the DMF device afforded transformation efficiency of $1.2 \times 10^6$ colony-forming units (CFU)/µg DNA (image A of FIG. 11), slightly higher than the benchtop method of heat shock, which generated a transformation efficiency of $9.6 \times 10$ CFU/µg DNA (image B of FIG. 1).

Unlike previous microfluidic systems, the DMF transformation device allows completely automated bacteria transformation and assay. This technology will be of great utility for systematic interpretation of gene delivery methods and high-throughput screening of gene variants with minimal reagent requirements.

Example 2

High Throughput Droplet Microfluidic Screening for Directed Evolution of Ionic Liquid Tolerance Droplet microfluidics today is carried out in two formats—droplets-in-flow and digital microfluidics. Droplets-in-flow method has much higher throughput but very poor control over droplet manipulation to accomplish tasks such as addition and sorting. Digital microfluidics (DMF), on the other hand, offers excellent control over droplet manipulation but has very limited throughput. Herein describes an architecture that combines the benefits of the two formats to overcome their respective inherent limitations. This example details the fundamental operation of this hybrid method, the functionality of three proof-of-concept devices developed thus far, and an application toward IL tolerance evolution.

"Droplets-in-flow" refers to the movement of aqueous droplets containing a wide range of reagents and samples in an immiscible carrier fluid such as fluorocarbon media. "DMF" refers to the movement of droplets via a dielectrophoretic force based upon electric field gradients.

FIG. 12 shows the fundamental designing procedure of the device. DMF electrodes are plated onto a glass slide, and then the electrodes are insulated with ~5 μm of dielectric. Channel features are built on top of the insulated electrodes, and then the top layer is covered to seal the channels.

FIG. 13 shows the basic operation of the device. (A) At this point the droplet feels the full hydrodynamic force of the flow. (B) Once the droplet reaches this region, the flow takes alternate paths, reducing the hydrodynamic force, allowing the dielectrophoretic force of the DMF electrodes to take over. Examples of reducing the hydrodynamic force in a channel by allowing alternate flow paths include a widening channel and side channels attached to the main channel. (C) When the droplet passes the alternate flow path area, the droplet feels the full flow rate and speeds along down the channel.

Figure 14:
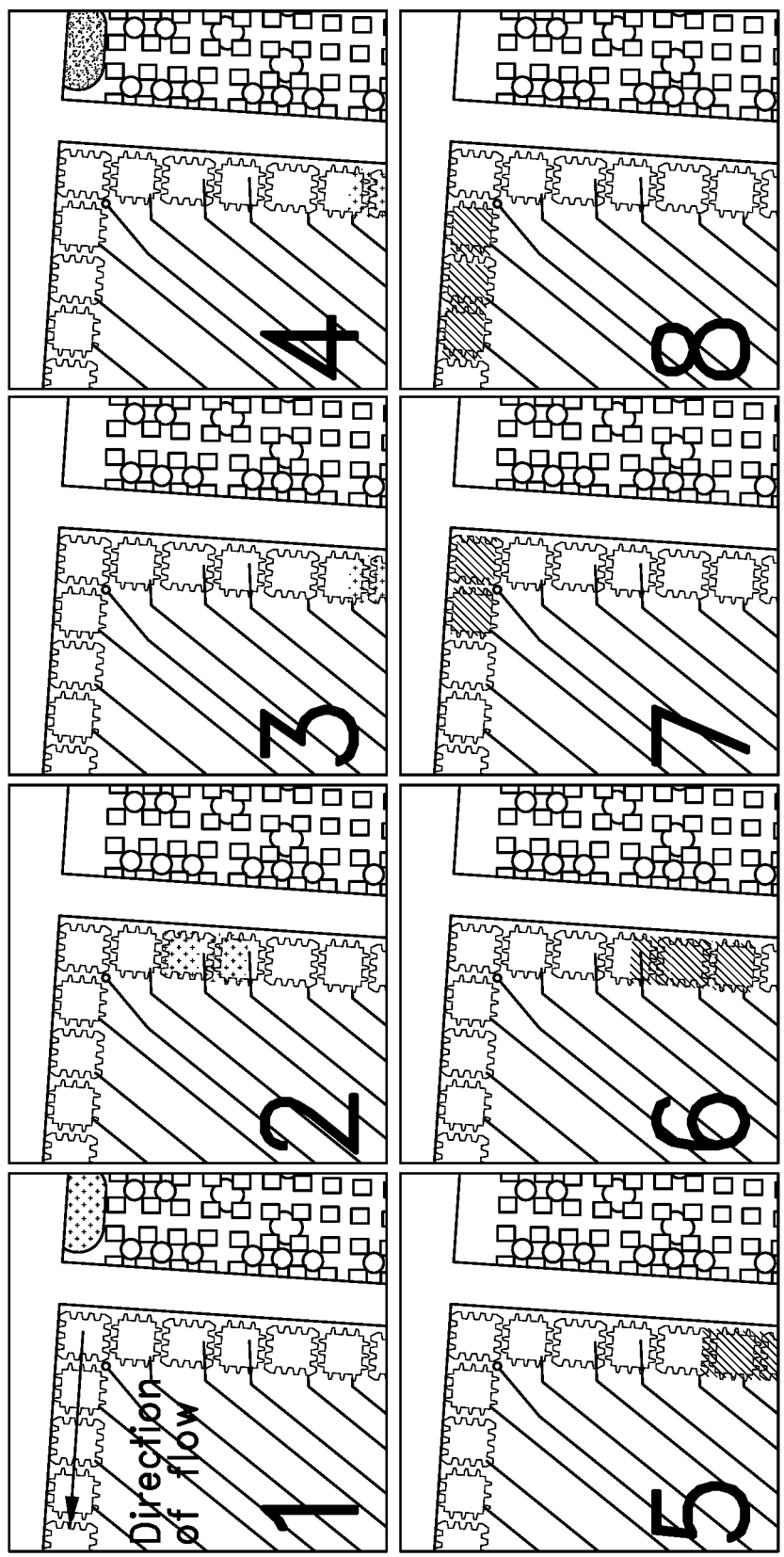
FIG. 14 shows a non-limiting operation sequence of the droplet merging device described herein.

FIG. 14 shows the operation sequence of the droplet merging device. When the $1^{st}$ droplet reaches the corner electrode, a change in resistance is detected and a sequence is initiated that directs the droplet into the bottom cavity (3). An identical operation occurs for the $2^{nd}$ droplet, where the two droplets merge at the bottom of the cavity. Upon merging, another sequence is initiated ejecting the droplet back into the flow.

Figure 15:
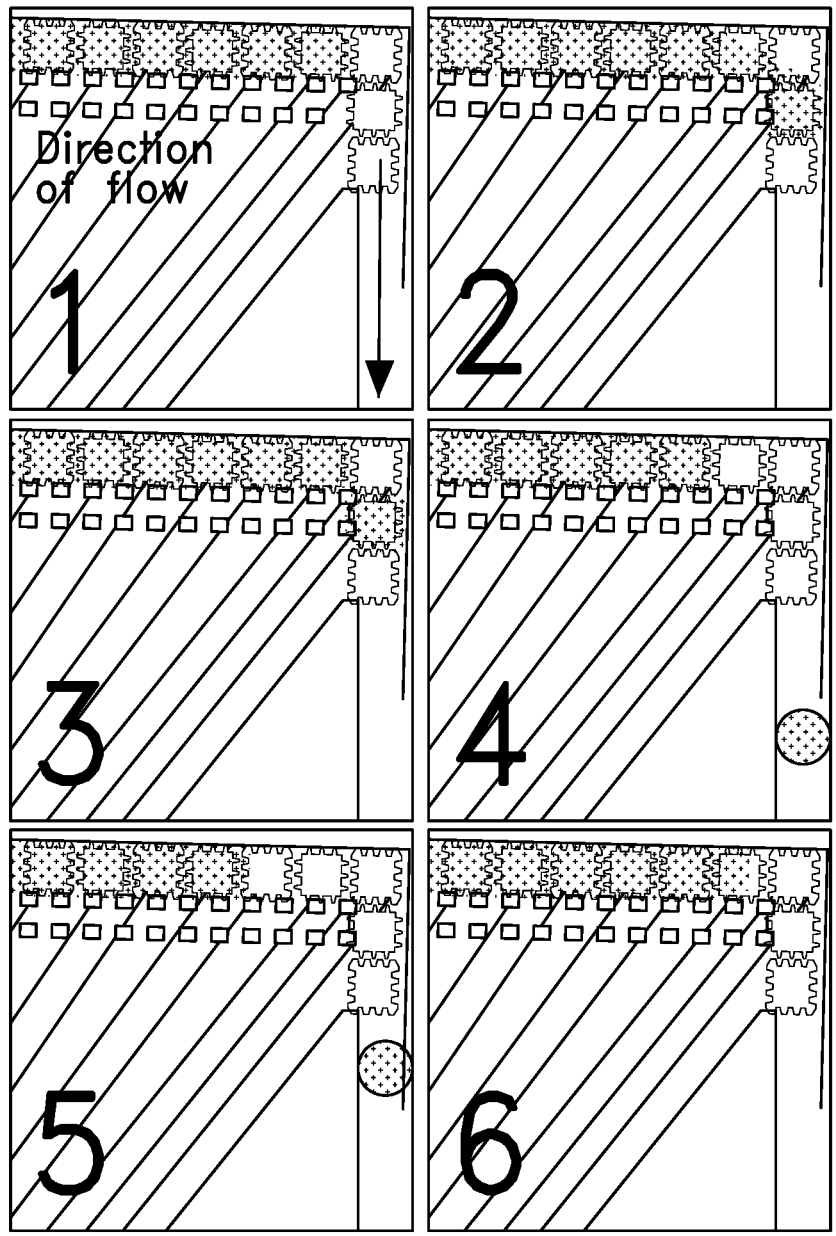
FIG. 15 shows a non-limiting example of on-demand droplet generation.

FIG. 15 shows on-demand droplet generation. A column of reagents (blue) remains static while flow passes in a perpendicular channel. A sequence is initiated using the electrodes to drag a droplet from the column into the perpendicular channel's flow. When the column is depleted (5), electrodes sense the change in resistance and a valve is opened to replenish (6).

Figure 16:
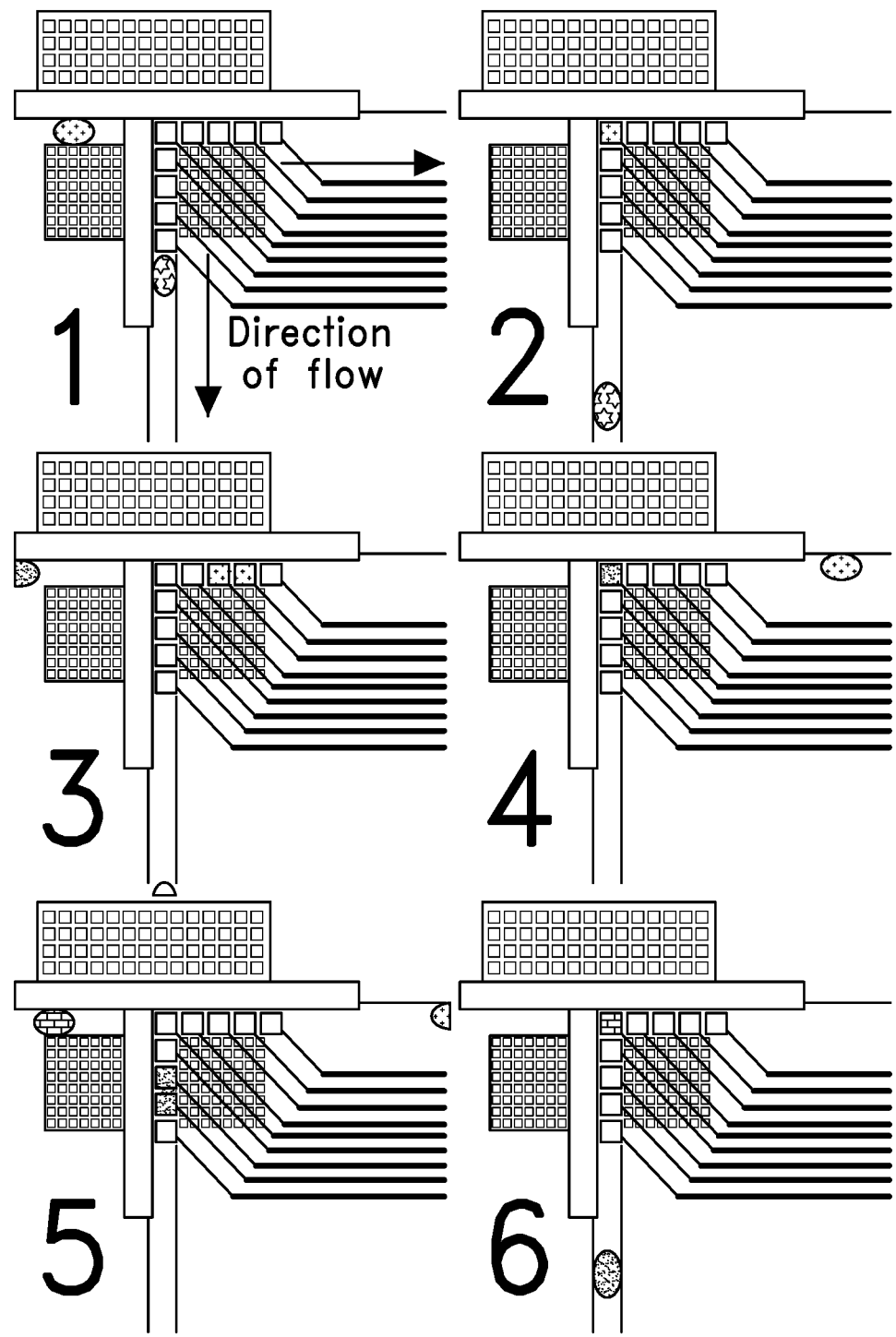
FIG. 16 shows a non-limiting operation sequence of a binary droplet sorter according to the disclosure herein.

FIG. 16 shows a binary droplet sorter. A transducer signal upstream (e.g., a PMT) measures an aspect of a passing droplet flowing from the left side of the figure and sends a signal to the sorter controller to decide what channel to send the droplet to. Once the droplet hits the first corner electrode, the decided sequence is initiated sending to the droplet to its respective channel.

FIG. 17 shows directed evolution of an ionic liquid (IL) tolerance. (A) shows the photo of the actual chip. (B) shows the schematic of the architecture and the function of the chip used for the directed evolution of IL tolerance. A droplet containing a colony derived from a single $E.$ $coli$ enters from a separate cell-incubating-chip. The bacteria droplet passes the reagent inlet electrodes, initiating formation of a reagent droplet with a time delay. Once the bacteria droplet hits the first corner electrode of the merging device, a sequence is initiated to seat the bacteria droplet. The same occurs for the following reagent droplet, where the two are then merged and subsequently ejected into the flow towards the serpentine kept at 65° C. The droplets then pass the detection point where a PMT detects the intensity of the fluorescent signal, telling the sorting device whether or not to send the droplet to the 'waste' or 'keep' channel.

Figure 18:
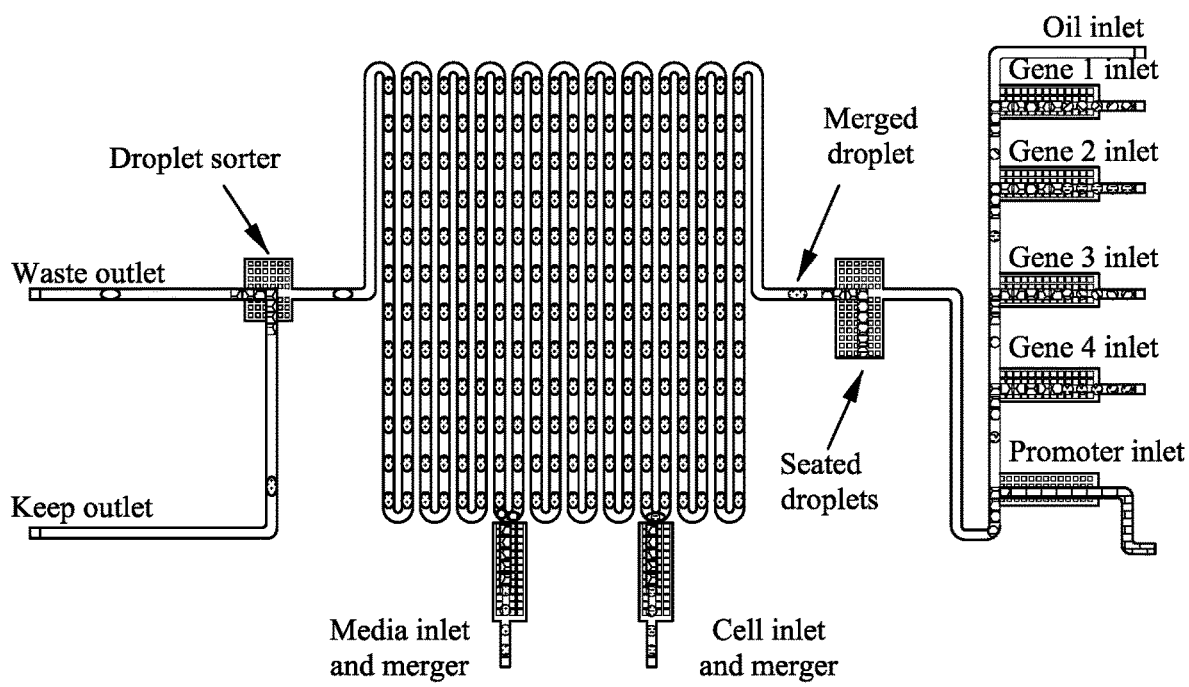
FIG. 18 shows a schematic of the architecture and the function of a chip used for DNA assembly, culture, and assay.

FIG. 18 shows the schematic of the architecture and the function of a chip used for DNA assembly, culture, and assay. In this device, cell and media inlet channels have alternating flow paths to slow down the droplets in the serpentine channel along with electrodes to capture and merge the DNA droplets and cell droplets. In other words, the cell and media inlet channels comprise droplet control channels. A droplet from the serpentine channel will be slowed down by the alternating flow paths and initially captured by the first electrode. Simultaneously, a droplet containing cells in added moved into the serpentine channel by the bottom electrodes. Actuation of the top electrodes allows droplet merger, and upon deactivation of the electrodes the droplets continue to flow down the serpentine channel.

The operation sequence of the device in FIG. 18 is as follows: droplets each of which contains different gene parts (Gene 1-4) or a promoter are introduced into different inlets (Gene 1-4 or promoter inlet) and merge together in the first droplet control channel; the merged nucleic acid droplets are incubated in a serpentine channel on chip at 65° C.; a droplet containing cells and the merged nucleic acid droplet merge in the second droplet control channel, and the merged DNA-cell droplets incubated in the serpentine channel at 65° C.; a droplet containing media and the merged DNA-cell droplet merge in the third droplet control channel, and the merged droplets are further incubated in the serpentine channel at 65° C.; after incubation, the droplets are sorted, and only droplets with desirable characteristics (e.g., high expression level) are collected.

Figure 19:
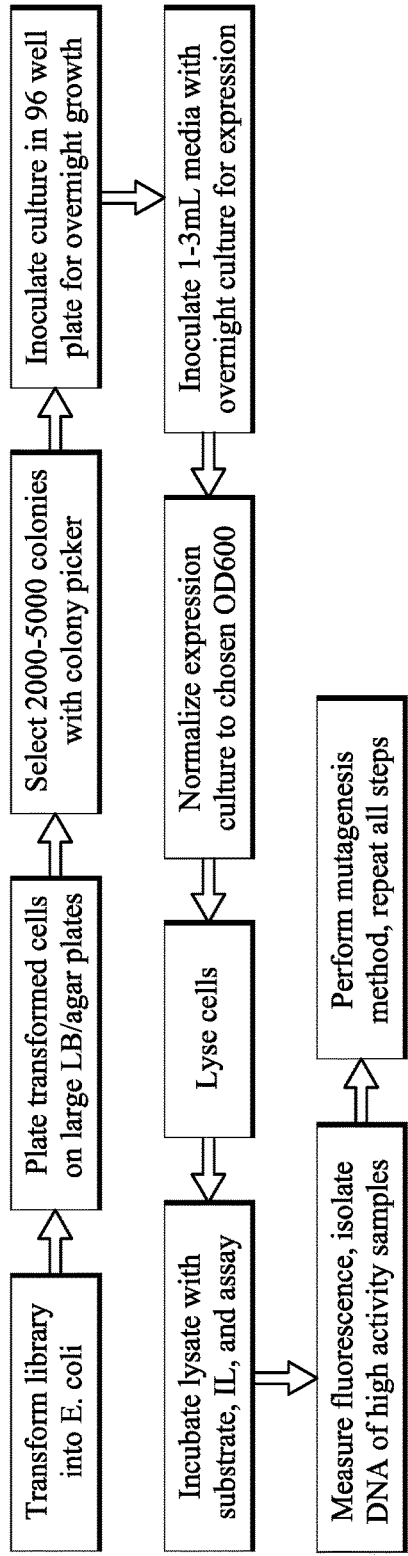
FIG. 19 is a flow chart for the conventional robotic method for high-throughput screening of IL tolerant *E. coli*.

FIG. 19 shows a flow chart for the conventional robotic method for high-throughput screening of IL tolerant $E.$ $coli$. Library is transformed into $E.$ $coli$ colonies, and 2000-5000 colonies are picked and cultured for expression. Then, fluorescence of cultured colonies is measured, and DNA with high activity is isolated. After performing mutagenesis on the selected DNA, all the steps above are repeated. These steps are conducted under an automated robotic system for high speed and efficiency.

Figure 20:
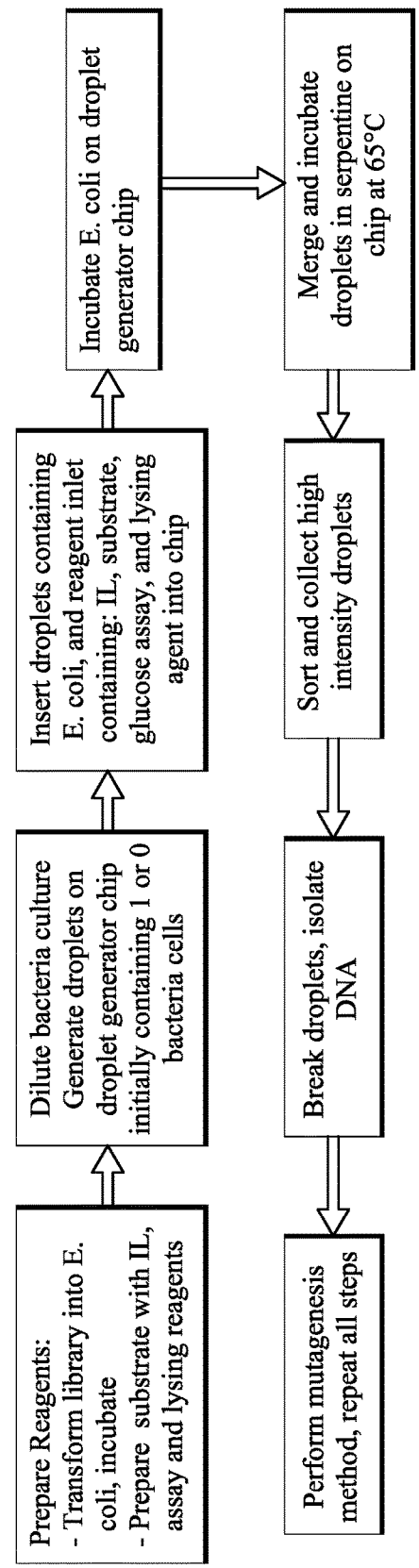
FIG. 20 is a flow chart for the microfluidic platform for high-throughput screening of IL tolerant *E. coli*.

FIG. 20 shows a flow chart for the microfluidic platform for high-throughput screening of IL tolerant $E.$ $coli$. Library is transformed into $E.$ $coli$ colonies, and the colonies are incubated. The cultures are used to generate bacteria droplets, each of which contains 1 or 0 bacteria cell. Bacteria droplets are incubated on a droplet generator chip in the bacteria inlet. In the reagent inlet, a mixture of IL, substrate, glucose assay, and lysing agent is introduced, and reagent droplets are generated from a separate droplet generator chip. Then, a bacterial droplet and a reagent droplet are merged in a droplet control apparatus, and the merged droplets are incubated in serpentine on chip at 65° C. After incubation, intensity of the merged droplets is measured, and only droplets with high intensities are collected. DNA in droplets with high intensities is then collected. After performing mutagenesis on the selected DNA, all the steps above are repeated.

Example 3

Off-Chip Sensing System for Droplet Tracking

Figure 22:
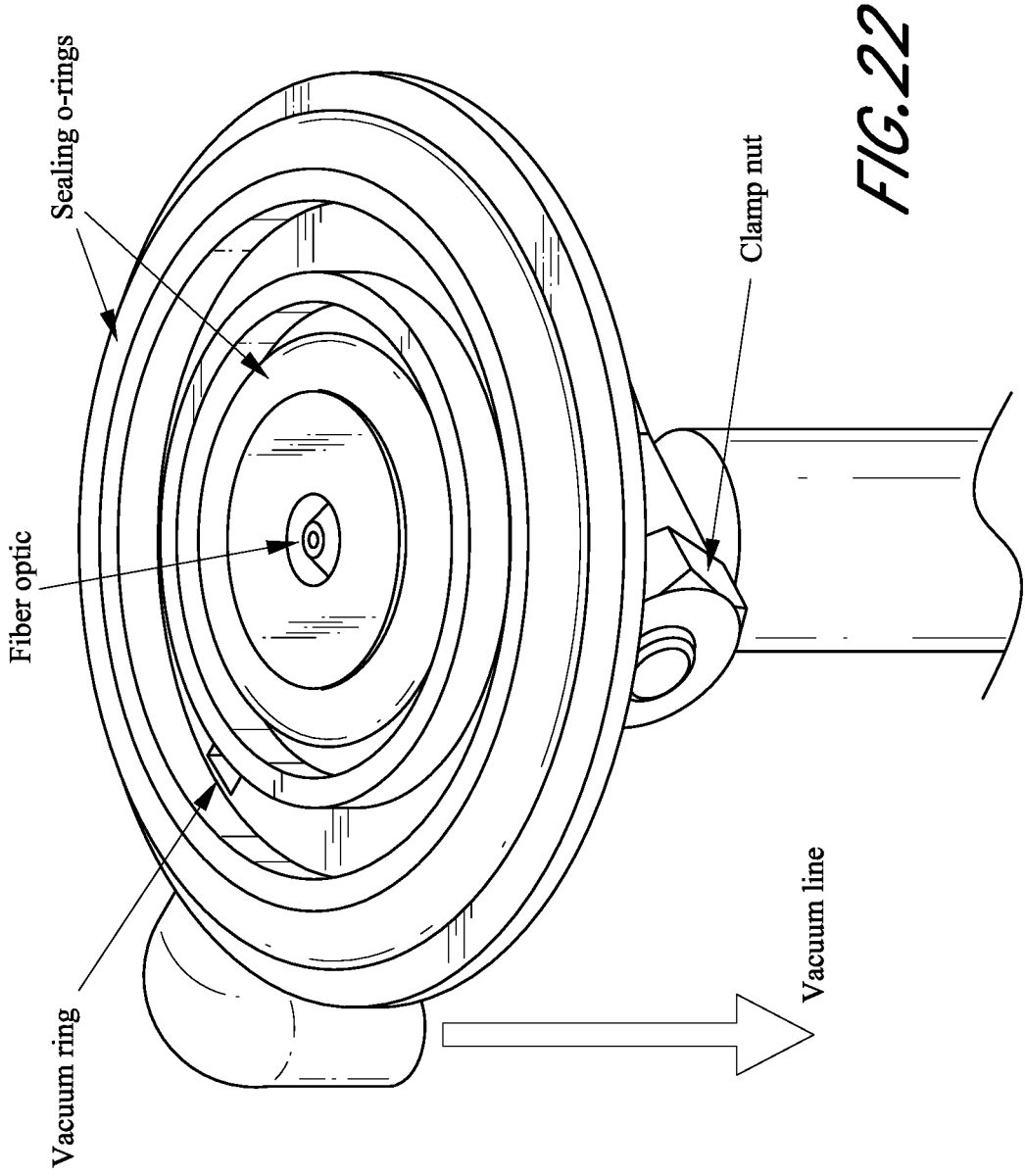
FIG. 22 is a schematic illustration of a 3D structure of the off-chip sensing system for droplet tracking according to the embodiments disclosed herein.
Figure 23:
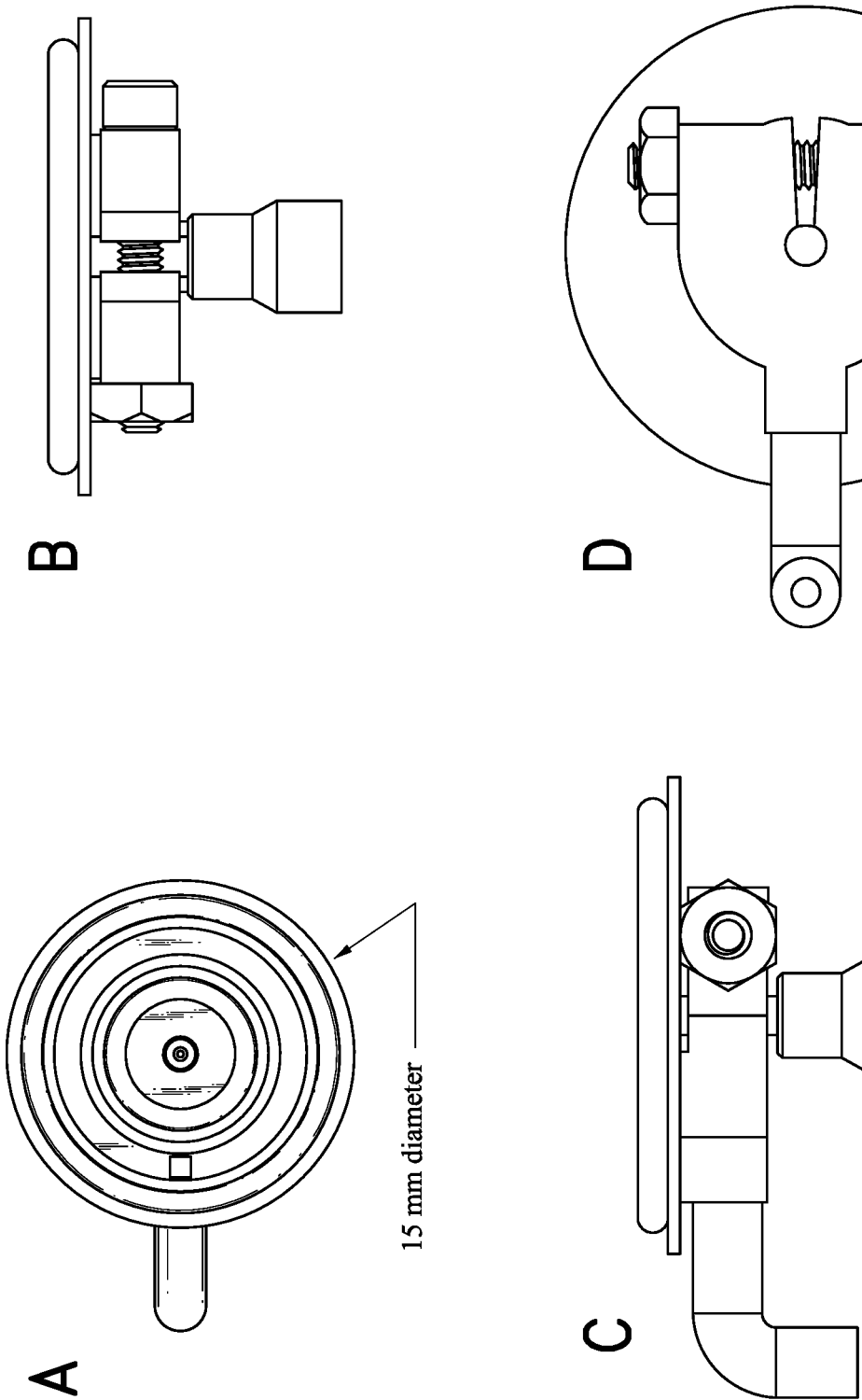
FIG. 23 shows top (A), side (B) and bottom views (C-D) of a non-limiting embodiment of the off-chip sensing system for droplet tracking according to the embodiments described herein.

The off-chip sensing system comprises 1) a specialized fiber optic positioning manifold to aid in droplet tracking, 2) clamp nut to hold the manifold, and 3) a vacuum ring, sealing O-rings and a vacuum line to maintain vacuum (FIGS. 22 and 23). The manifold is placed directly under the channel where the droplets will be passing. A vacuum seal created and maintained by a vacuum ring, sealing O-rings, and a vacuum line is used to hold the manifold in place making relocation and exact positioning of the fiber simple and fast. This allows for versatile droplet tracking at multiple locations on the device without redesigning or fabrication of a new chip, offering no obstruction to chip design. The sensor relies on a fiber optic cable connected to a PMT to detect the partial blockage of light when a droplet passes under the light source. A photomultiplier tube (PMT) records the wavelength and intensity of the droplet's absorbance or fluorescence (or other detector/metric), and the signals recorded by the PMT can be used to determine the presence of a droplet, the length of the droplet, and flow rate depending on where the fiber optic is placed.

FIG. 24 demonstrates droplet tracking using the off-chip sensing system. Panel A of FIG. 24 shows actual data gathered via a PMT showing the detection of the droplet shadow. Panel B of FIG. 24 shows a diagram showing the fundament operation of the droplet detection. Once a droplet passes over the fiber optic cable, the interface of the droplet blocks light emitted from the light source and detected by the fiber optic, and such blockage of light creates a dip in signal. Immediately afterwards, a bright spot on the droplet in which the light is focused by the convex shape of the droplet creates a peak in signal, followed by a reading that indicates the amount of light going through bulk of the droplet. This peak-valley occurs for each end of the droplet, indicating the start and end of each passing droplet.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone. A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be appar-

What we claim is:

1. A microfluidic device comprising:
a droplet-generating means comprising one or more droplet channels,
wherein the droplet-generating means is configured to merge two immiscible fluids to generate droplets in at least one of the one or more droplet channels, and
wherein the droplets generated from the droplet-generating means are about 1 pL to about 1 mL in volume;
a droplet control apparatus comprising a plurality of electrodes and one or more channels,
wherein the droplet control apparatus is in fluid communication with the droplet-generating means,
wherein the plurality of electrodes is on the floor, the ceiling, or both of the one or more channels in the droplet control apparatus,
wherein the plurality of electrodes are positioned downstream from the droplet-generating means in the flow path of the droplets,
wherein the plurality of electrodes is configured to guide the movement of droplets through the droplet control apparatus, and
wherein the plurality of electrodes comprises at least five electrodes and each electrode in the plurality of electrodes is adjacent to at least one other electrode within the plurality of electrodes, thereby forming a grid of electrodes; and
a flow control means in fluid communication with the droplet-generating means or droplet control apparatus or both,
wherein the flow control means is configured to alter the flow rate of the droplets in the microfluidic device,
wherein the flow control means comprises one or more obstacles,
wherein the obstacle is a post or a plurality of posts, a pillar or a plurality of pillars, a ramp, a bump, a droplet, or a combination thereof,
wherein the one or more obstacles are positioned upstream from the plurality of electrodes in the flow path of the droplets, and
wherein the one or more obstacles are configured to reduce the speed of the droplets, thereby enabling the plurality of electrodes to guide the movement of droplets having reduced speed.

2. The device according to claim 1, wherein the droplet-generating means comprises a vacuum, a hydrodynamic flow generator, a hydrodynamic pressure generator, or any combination thereof.

3. The device according to claim 1, wherein at least one of the two immiscible fluids is aqueous.

4. The device according to claim 1, wherein at least one of the two immiscible fluids comprises oil.

5. The device according to claim 1, wherein droplets generated from the droplet-generating means are substantially uniform in size.

6. The device according to claim 1, wherein the flow control means comprises one or more valves, one or more pumps, or any combination thereof.

7. The device according to claim 1, wherein the flow control means comprises a channel or a portion of a channel that is widening.

8. The device according to claim 1, wherein the flow control means comprises a channel or a portion of a channel that is constricting.

9. The device according to claim 1, further comprising at least one inlet channel connected to the one or more droplet channels.

10. The device according to claim 9, wherein the droplet-generating means comprises at least one channel connected to the at least one inlet channel.

11. The device according to claim 1, wherein the droplet-generating means comprises at least one channel connected to the droplet control apparatus.

12. The device according to claim 1, further comprising at least one heating pad.

13. The device according to claim 1, further comprising an incubation apparatus.

14. The device according to claim 1, further comprising an additional layer of electrodes.

15. The device according to claim 1, wherein the flow control means comprises alternate flow paths.

* * * * *